US012257436B2

(12) United States Patent
Gururaj et al.

(10) Patent No.: US 12,257,436 B2
(45) Date of Patent: Mar. 25, 2025

(54) NEURAL SENSING IN AN IMPLANTABLE STIMULATOR DEVICE DURING PASSIVE CHARGE RECOVERY

(71) Applicant: Boston Scientific Neuromodulation Corporation, Valencia, CA (US)

(72) Inventors: Kiran K. Gururaj, Valencia, CA (US); David M. Wagenbach, Simi Valley, CA (US); Philip L. Weiss, Sherman Oaks, CA (US); Emanuel Feldman, Simi Valley, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 454 days.

(21) Appl. No.: 17/597,799

(22) PCT Filed: Aug. 4, 2020

(86) PCT No.: PCT/US2020/044881
§ 371 (c)(1),
(2) Date: Jan. 24, 2022

(87) PCT Pub. No.: WO2021/026151
PCT Pub. Date: Feb. 11, 2021

(65) Prior Publication Data
US 2022/0233866 A1 Jul. 28, 2022

Related U.S. Application Data

(60) Provisional application No. 62/883,452, filed on Aug. 6, 2019.

(51) Int. Cl.
*A61N 1/36* (2006.01)
*A61B 5/00* (2006.01)
(Continued)

(52) U.S. Cl.
CPC .......... *A61N 1/36125* (2013.01); *A61B 5/388* (2021.01); *A61B 5/4058* (2013.01);
(Continued)

(58) Field of Classification Search
CPC ............ A61N 1/36125; A61N 1/36135; A61N 1/36146
See application file for complete search history.

(56) References Cited

U.S. PATENT DOCUMENTS 5,697,958 A   12/1997  Paul et al.
5,702,429 A   12/1997  King
(Continued)

FOREIGN PATENT DOCUMENTS

WO    2015/077362    5/2015
WO    2017/100866    6/2017
(Continued)

OTHER PUBLICATIONS

H. Mino & J. Rubenstein, "Effects of Neural Refractoriness on Spatio-Temporal Variability in Spike Initiations with Eletrical Stimulation," IEEE Trans. On Neural Sys. & Rehabilitation Eng., vol. 14, No. 3, pp. 273-280 (2006).
(Continued)

*Primary Examiner* — Tammie K Marlen
*Assistant Examiner* — Maria Catherine Anthony
(74) *Attorney, Agent, or Firm* — Lewis & Reese, PLLC

(57) ABSTRACT

Techniques for sensing neural responses such as Evoked Compound Action Potentials (ECAPs) in an implantable stimulator device are disclosed. A first therapeutic pulse phase is followed by a charge recovery phase that includes at least one high-impedance passive charge recovery duration. The ECAP is sensed during the high-impedance passive charge recovery duration. The time period of the passive charge recovery is lengthened and the high-impedance pas-
(Continued)

sive recharge duration entirely overlaps the ECAP (i.e., the neural response duration) at the sensing electrode.

5 Claims, 10 Drawing Sheets

(51) Int. Cl.
*A61B 5/388* (2021.01)
*A61N 1/02* (2006.01)

(52) U.S. Cl.
CPC ......... *A61N 1/025* (2013.01); *A61N 1/36135* (2013.01); *A61N 1/36146* (2013.01)

(56) References Cited

U.S. PATENT DOCUMENTS

| | | | |
|---|---|---|---|
| 5,902,236 A | 5/1999 | Iversen | |
| 5,902,249 A | 5/1999 | Lyster | |
| 5,913,882 A | 6/1999 | King | |
| 6,181,969 B1 | 1/2001 | Gord et al. | |
| 6,516,227 B1* | 2/2003 | Meadows | A61N 1/37247 607/46 |
| 7,024,247 B2 | 4/2006 | Gliner et al. | |
| 7,424,322 B2 | 9/2008 | Lombardi et al. | |
| 7,450,992 B1 | 11/2008 | Cameron | |
| 8,255,057 B2 | 8/2012 | Fang et al. | |
| 8,335,664 B2 | 12/2012 | Eberle | |
| 8,352,030 B2 | 1/2013 | Denison | |
| 8,606,362 B2 | 12/2013 | He et al. | |
| 8,620,436 B2 | 12/2013 | Parramon et al. | |
| 9,044,155 B2 | 6/2015 | Strahl | |
| 9,155,892 B2 | 10/2015 | Parker et al. | |
| 9,248,274 B2 | 2/2016 | Troosters et al. | |
| 9,248,279 B2* | 2/2016 | Chen | A61N 1/36146 |
| 9,265,431 B2 | 2/2016 | Hincapie Ordonez et al. | |
| 9,302,112 B2 | 4/2016 | Bornzin et al. | |
| 9,381,356 B2 | 7/2016 | Parker et al. | |
| 9,386,934 B2 | 7/2016 | Parker et al. | |
| 9,403,013 B2 | 8/2016 | Walker et al. | |
| 9,409,020 B2 | 8/2016 | Parker | |
| 9,526,897 B2 | 12/2016 | Chen et al. | |
| 9,533,148 B2 | 1/2017 | Carcieri et al. | |
| 9,731,116 B2 | 8/2017 | Chen | |
| 9,872,990 B2 | 1/2018 | Parker et al. | |
| 9,974,455 B2 | 5/2018 | Parker et al. | |
| 10,076,667 B2 | 9/2018 | Kaula et al. | |
| 10,881,859 B2 | 1/2021 | Brill et al. | |
| 10,926,092 B2 | 2/2021 | Esteller et al. | |
| 2002/0156513 A1 | 10/2002 | Borkan | |
| 2005/0246004 A1 | 11/2005 | Cameron et al. | |
| 2008/0146894 A1 | 6/2008 | Bulkes et al. | |
| 2012/0092031 A1 | 4/2012 | Shi et al. | |
| 2012/0095519 A1 | 4/2012 | Parramon et al. | |
| 2012/0095529 A1 | 4/2012 | Parramon et al. | |
| 2013/0289665 A1 | 10/2013 | Marnfeldt et al. | |
| 2014/0194772 A1 | 7/2014 | Single et al. | |
| 2014/0236042 A1 | 8/2014 | Parker et al. | |
| 2014/0296737 A1 | 10/2014 | Parker et al. | |
| 2015/0119751 A1 | 4/2015 | Stanslaski et al. | |
| 2015/0157861 A1 | 6/2015 | Aghassian et al. | |
| 2015/0282725 A1 | 10/2015 | Single et al. | |
| 2015/0313487 A1 | 11/2015 | Single et al. | |
| 2016/0166164 A1 | 6/2016 | Obradovic et al. | |
| 2016/0220820 A1 | 8/2016 | Zottola | |
| 2016/0287126 A1 | 10/2016 | Parker et al. | |
| 2016/0287182 A1 | 10/2016 | Single et al. | |
| 2017/0049345 A1 | 2/2017 | Single et al. | |
| 2017/0071490 A1 | 3/2017 | Parker et al. | |
| 2017/0135624 A1 | 5/2017 | Parker et al. | |
| 2017/0216587 A1 | 8/2017 | Parker et al. | |
| 2017/0296823 A1 | 10/2017 | Hershey et al. | |
| 2017/0361101 A1 | 12/2017 | Single et al. | |
| 2018/0071527 A1* | 3/2018 | Feldman | A61N 1/05 |
| 2018/0110987 A1 | 4/2018 | Parker et al. | |
| 2018/0117335 A1 | 5/2018 | Parker et al. | |
| 2018/0132747 A1 | 5/2018 | Parker et al. | |
| 2018/0132760 A1 | 5/2018 | Parker et al. | |
| 2018/0133459 A1 | 5/2018 | Parker et al. | |
| 2018/0140831 A1 | 5/2018 | Feldman et al. | |
| 2018/0228391 A1 | 8/2018 | Parker et al. | |
| 2018/0228547 A1 | 8/2018 | Parker et al. | |
| 2018/0256052 A1 | 9/2018 | Parker et al. | |
| 2019/0099602 A1 | 4/2019 | Esteller et al. | |
| 2019/0275331 A1 | 9/2019 | Zhu | |
| 2019/0290900 A1 | 9/2019 | Esteller et al. | |
| 2019/0299006 A1 | 10/2019 | Marnfeldt | |
| 2019/0366094 A1 | 12/2019 | Esteller et al. | |
| 2020/0155019 A1 | 5/2020 | Esteller et al. | |
| 2020/0305745 A1 | 10/2020 | Wagenbach et al. | |

FOREIGN PATENT DOCUMENTS

| | | |
|---|---|---|
| WO | 2017/173493 | 10/2017 |
| WO | 2017/210352 | 12/2017 |
| WO | 2017/219096 | 12/2017 |

OTHER PUBLICATIONS

M. Moffit et al., A Novel 3-Dimensional Algorithm for Model-Based Programming in Spinal Cord Stimuation (SCS): Illumina-3D™, presentation (2013).

M. Hughes, "Fundamentals of Clinical ECAP Measures in Cochlear Implants: Part 1: Use of the ECAP in Speech Processor Programming (2nd Ed.)," Audiology Online (Nov. 8, 2010) (http://www.audiologyonline.com/articles/fundamentalsclinicalecapmeasuresin846).

I. Akhoun et al., "Electrically evoked compound action potential artifact rejection by independent component analysis: Technique validation," Hearing Research 302, pp. 60-73 (2013).

J. Rubinstein et al., "Pseudospontaneous activity: stochastic independence of auditory nerve fibers with electrical stimulation," Hear Res., 127(1-2), pp. 108-118 (1999) (abstract only).

J. Paz, "Physiological Midline Mapping Based on Spinal Cord Stimulation (SCS) Response Using the 32-Contact Paddle Lead," 19th NANS Annual Meeting (Dec. 13-15, 2015).

E.L. Air et al., "Electrophysiologic Monitoring for Placement of Laminectomy Leads for Spinal Cord Stimulation Under General Anesthesia," Neuromodulation: Technology at the Neural Interface, vol. 15(6), pp. 573-580 (2012).

J.L. Shils et al., "Intraoperative Neurophysiologic Methods for Spinal Cord Stimulator Placement Under General Anesthesia," Neuromodulation: Technology at the Neural Interface, vol. 15(6), pp. 560-572 (2012).

A. Taghva et al., "Intraoperative Electromyography as an Adjunct to Sacral Neuromodulation for Chronic Pelvic Pain," Neuromodulation: Technology at the Neural Interface, vol. 18(1), pp. 62-66 (2015).

International Search Report and Written Opinion regarding corresponding PCT Application No. PCT/US2020/044881, mailed Oct. 15, 2020.

First Office Action regarding corresponding Chinese Patent Application No. 202080069764.X, mailed Jul. 4, 2024.

* cited by examiner

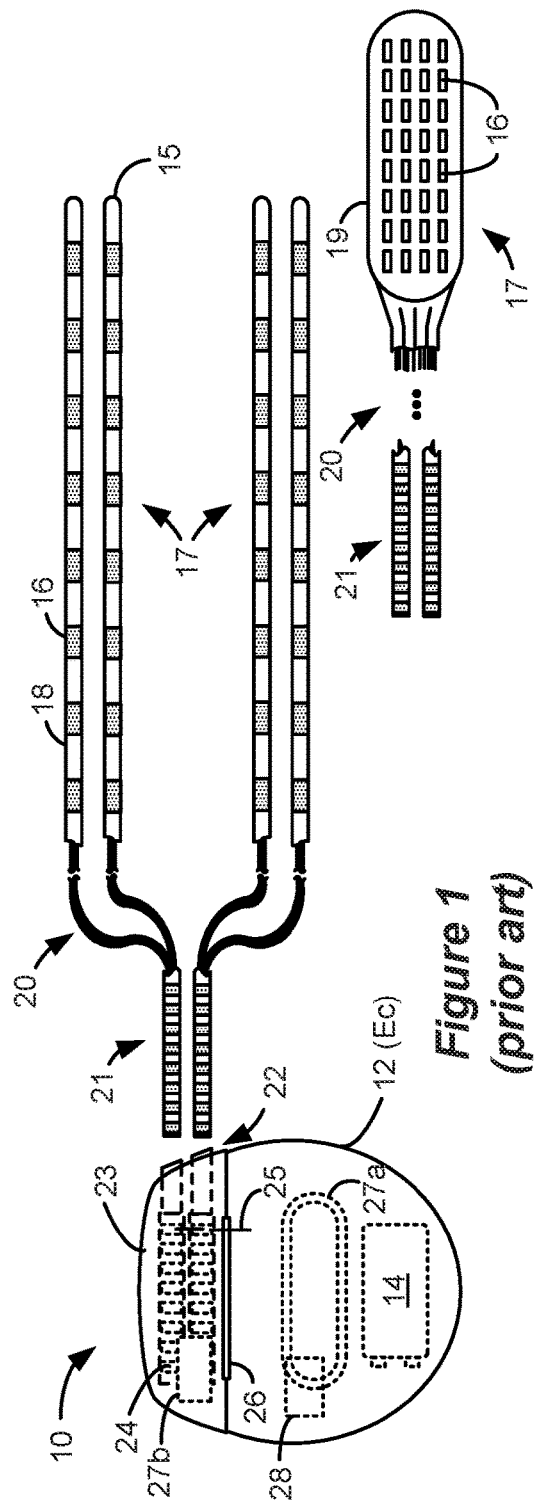
*Figure 1 (prior art)*
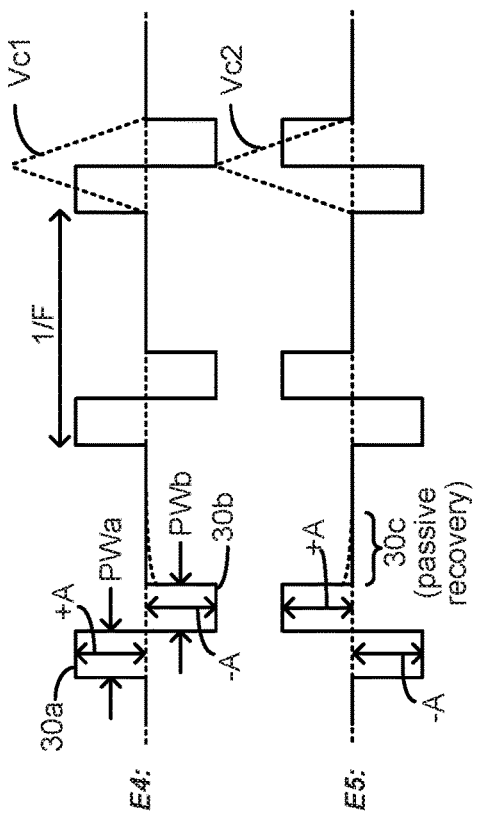
*Figure 2A (prior art)*
*Figure 2B (prior art)*

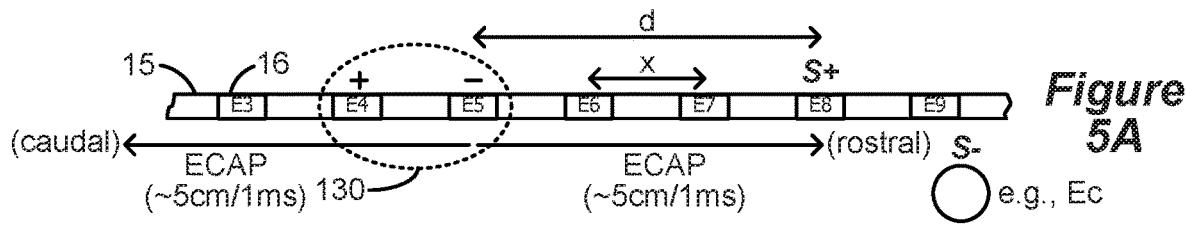
*Figure 5A*
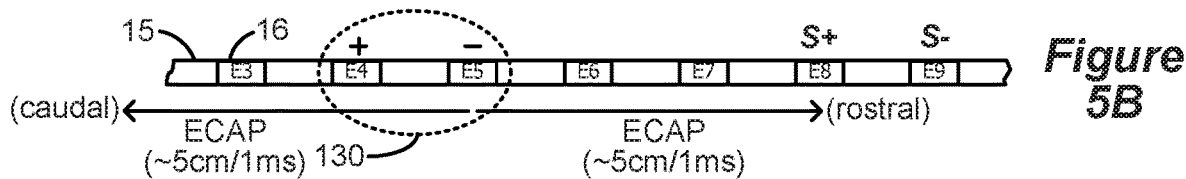
*Figure 5B*
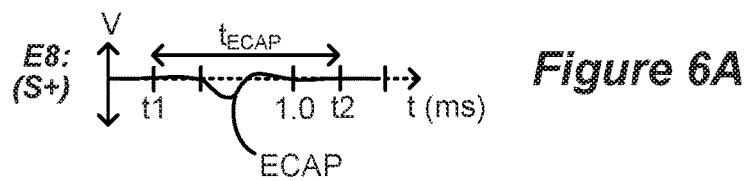
*Figure 6A*
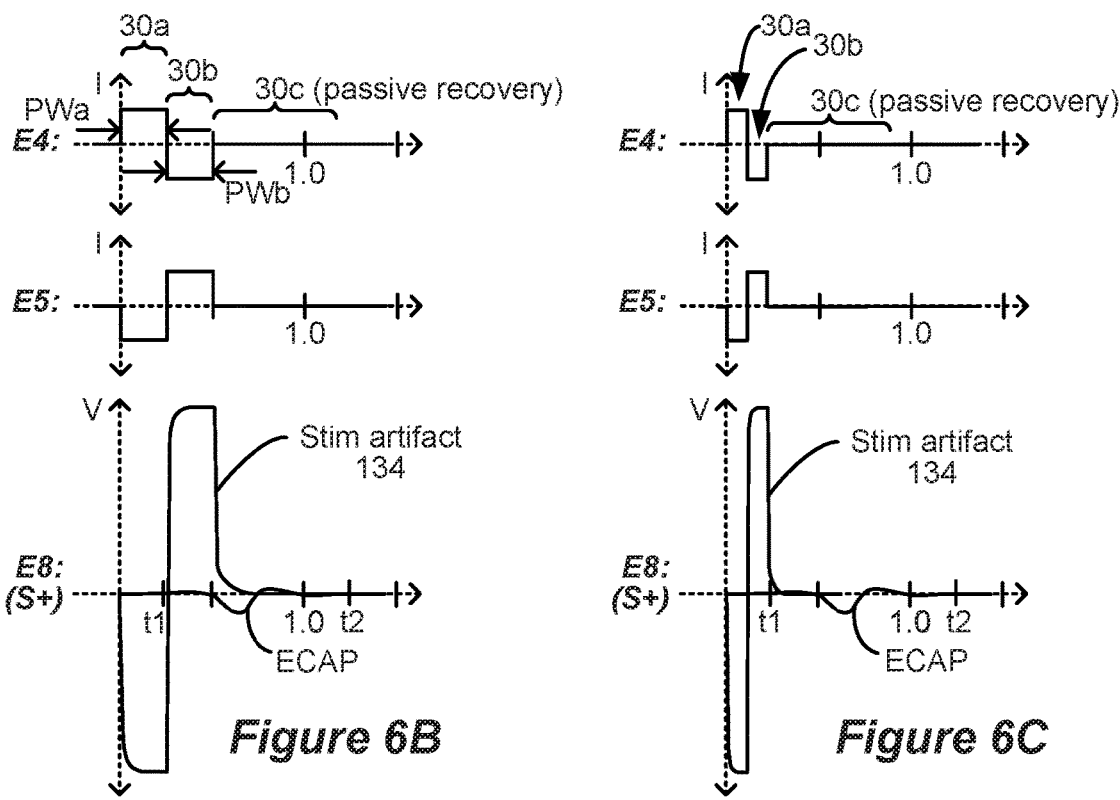
*Figure 6B*  *Figure 6C*

NEURAL SENSING IN AN IMPLANTABLE STIMULATOR DEVICE DURING PASSIVE CHARGE RECOVERY

FIELD OF THE INVENTION

This application relates to Implantable Medical Devices (IMDs), and more specifically to circuitry to assist with sensing neural signals in an implantable stimulator device.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable neurostimulator device system.

An SCS system typically includes an Implantable Pulse Generator (IPG) 10 shown in FIG. 1. The IPG 10 includes a biocompatible device case 12 that holds the circuitry and a battery 14 for providing power for the IPG to function. The IPG 10 is coupled to tissue-stimulating electrodes 16 via one or more electrode leads that form an electrode array 17. For example, one or more percutaneous leads 15 can be used having ring-shaped or split-ring electrodes 16 carried on a flexible body 18. In another example, a paddle lead 19 provides electrodes 16 positioned on one of its generally flat surfaces. Lead wires 20 within the leads are coupled to the electrodes 16 and to proximal contacts 21 insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12.

In the illustrated IPG 10, there are thirty-two electrodes (E1-E32), split between four percutaneous leads 15, or contained on a single paddle lead 19, and thus the header 23 may include a 2×2 array of eight-electrode lead connectors 22. However, the type and number of leads, and the number of electrodes, in an IPG is application specific and therefore can vary. The conductive case 12 can also comprise an electrode (Ec). In a SCS application, the electrode lead(s) are typically implanted in the spinal column proximate to the dura in a patient's spinal cord, preferably spanning left and right of the patient's spinal column. The proximal contacts 21 are tunneled through the patient's tissue to a distant location such as the buttocks where the IPG case 12 is implanted, at which point they are coupled to the lead connectors 22. In other IPG examples designed for implantation directly at a site requiring stimulation, the IPG can be lead-less, having electrodes 16 instead appearing on the body of the IPG 10 for contacting the patient's tissue. The IPG lead(s) can be integrated with and permanently connected to the IPG 10 in other solutions. The goal of SCS therapy is to provide electrical stimulation from the electrodes 16 to alleviate a patient's symptoms, such as chronic back pain.

IPG 10 can include an antenna 27a allowing it to communicate bi-directionally with a number of external devices used to program or monitor the IPG, such as a hand-held patient controller or a clinician's programmer, as described for example in U.S. Patent Application Publication 2019/0175915. Antenna 27a as shown comprises a conductive coil within the case 12, although the coil antenna 27a can also appear in the header 23. When antenna 27a is configured as a coil, communication with external devices preferably occurs using near-field magnetic induction. IPG 10 may also include a Radio-Frequency (RF) antenna 27b. In FIG. 1, RF antenna 27b is shown within the header 23, but it may also be within the case 12. RF antenna 27b may comprise a patch, slot, or wire, and may operate as a monopole or dipole. RF antenna 27b preferably communicates using far-field electromagnetic waves, and may operate in accordance with any number of known RF communication standards, such as Bluetooth, Zigbee, MICS, and the like.

Stimulation in IPG 10 is typically provided by pulses each of which may include a number of phases such as 30a and 30b, as shown in the example of FIG. 2A. Stimulation parameters typically include amplitude (current I, although a voltage amplitude V can also be used); frequency (F); pulse width (PW) of the pulses or of its individual phases; the electrodes 16 selected to provide the stimulation; and the polarity of such selected electrodes, i.e., whether they act as anodes that source current to the tissue or cathodes that sink current from the tissue. These and possibly other stimulation parameters taken together comprise a stimulation program that the stimulation circuitry 28 in the IPG 10 can execute to provide therapeutic stimulation to a patient.

In the example of FIG. 2A, electrode E4 has been selected as an anode (during its first phase 30a), and thus provides pulses which source a positive current of amplitude +A to the tissue. Electrode E5 has been selected as a cathode (again during first phase 30a), and thus provides pulses which sink a corresponding negative current of amplitude −A from the tissue. This is an example of bipolar stimulation, in which only two lead-based electrodes are used to provide stimulation to the tissue (one anode, one cathode). However, more than one electrode may be selected to act as an anode at a given time, and more than one electrode may be selected to act as a cathode at a given time.

IPG 10 as mentioned includes stimulation circuitry 28 to form prescribed stimulation at a patient's tissue. FIG. 3 shows an example of stimulation circuitry 28, which includes one or more current source circuits $40_i$ and one or more current sink circuits $42_i$. The sources and sinks $40_i$ and $42_i$ can comprise Digital-to-Analog converters (DACs), and may be referred to as PDACs $40_i$ and NDACs $42_i$ in accordance with the Positive (sourced, anodic) and Negative (sunk, cathodic) currents they respectively issue. In the example shown, a NDAC/PDAC $40_i/42_i$ pair is dedicated (hardwired) to a particular electrode node ei 39. Each electrode node ei 39 is connected to an electrode Ei 16 via a DC-blocking capacitor Ci 38, for the reasons explained below. The stimulation circuitry 28 in this example also supports selection of the conductive case 12 as an electrode (Ec 12), which case electrode is typically selected for monopolar stimulation. PDACs $40_i$ and NDACs $42_i$ can also comprise voltage sources.

Proper control of the PDACs $40_i$ and NDACs $42_i$ allows any of the electrodes 16 to act as anodes or cathodes to create a current through a patient's tissue, R, hopefully with good therapeutic effect. In the example shown (FIG. 2A), and during the first phase 30a in which electrodes E4 and E5 are selected as an anode and cathode respectively, PDAC 404 and NDAC 425 are activated and digitally programmed to produce the desired current, A, with the correct timing (e.g., in accordance with the prescribed frequency F and pulse widths PWa). During the second phase 30b (PWb), PDAC 405 and NDAC 424 would be activated to reverse the polarity of the current. More than one anode electrode and more than one cathode electrode may be selected at one time, and thus current can flow through the tissue R between two or more of the electrodes 16.

Power for the stimulation circuitry 28 is provided by a compliance voltage VH. As described in further detail in U.S. Patent Application Publication 2013/0289665, the compliance voltage VH can be produced by a compliance voltage generator 29, which can comprise a circuit used to boost the battery 14's voltage (Vbat) to a voltage VH sufficient to drive the prescribed current A through the tissue R. The compliance voltage generator 29 may comprise an inductor-based boost converter as described in the '665 Publication, or can comprise a capacitor-based charge pump. Because the resistance of the tissue is variable, VH may also be variable, and can be as high as 18 Volts in one example.

Other stimulation circuitries 28 can also be used in the IPG 10. In an example not shown, a switching matrix can intervene between the one or more PDACs $40_i$ and the electrode nodes ei 39, and between the one or more NDACs $42_i$ and the electrode nodes. Switching matrices allows one or more of the PDACs or one or more of the NDACs to be connected to one or more anode or cathode electrode nodes at a given time. Various examples of stimulation circuitries can be found in U.S. Pat. Nos. 6,181,969, 8,606,362, 8,620,436, U.S. Patent Application Publications 2018/0071520 and 2019/0083796. Much of the stimulation circuitry 28 of FIG. 3, including the PDACs $40_i$ and NDACs $42_i$, the switch matrices (if present), and the electrode nodes ei 39 can be integrated on one or more Application Specific Integrated Circuits (ASICs), as described in U.S. Patent Application Publications 2012/0095529, 2012/0092031, and 2012/0095519, which are incorporated by reference. As explained in these references, ASIC(s) may also contain other circuitry useful in the IPG 10, such as telemetry circuitry (for interfacing off chip with telemetry antennas 27a and/or 27b), the compliance voltage generator 29, various measurement circuits, etc.

Also shown in FIG. 3 are DC-blocking capacitors Ci 38 placed in series in the electrode current paths between each of the electrode nodes ei 39 and the electrodes Ei 16 (including the case electrode Ec 12). The DC-blocking capacitors 38 act as a safety measure to prevent DC current injection into the patient, as could occur for example if there is a circuit fault in the stimulation circuitry 28. The DC-blocking capacitors 38 are typically provided off-chip (off of the ASIC(s)), and instead may be provided in or on a circuit board in the IPG 10 used to integrate its various components, as explained in U.S. Patent Application Publication 2015/0157861.

Although not shown, circuitry in the IPG 10 including the stimulation circuitry 28 can also be included in an External Trial Stimulator (ETS) device which is used to mimic operation of the IPG during a trial period and prior to the IPG 10's implantation. An ETS device is typically used after the electrode array 17 has been implanted in the patient. The proximal ends of the leads in the electrode array 17 pass through an incision in the patient and are connected to the externally-worn ETS, thus allowing the ETS to provide stimulation to the patient during the trial period. Further details concerning an ETS device are described in U.S. Pat. No. 9,259,574 and U.S. Patent Application Publication 2019/0175915.

Referring again to FIG. 2A, the stimulation pulses as shown are biphasic, with each pulse at each electrode comprising a first phase 30a followed thereafter by a second phase 30b of opposite polarity. (Although not shown, but as is well known, a short interphase period may intervene between the phases 30a and 30b during which no current is actively driven by the DAC circuitry 40/42, which allows the DAC circuitry time to transition between the phases). Biphasic pulses are useful to actively recover any charge that might be stored on capacitive elements in the electrode current paths, such as the DC-blocking capacitors 38, the electrode/tissue interface, or within the tissue itself. To recover all charge by the end of the second pulse phase 30b of each pulse (Vc4=Vc5=0V), the first and second phases 30a and 30b are preferably charged balanced at each electrode, with the phases comprising an equal amount of charge but of the opposite polarity. In the example shown, such charge balancing is achieved by using the same pulse width (PWa=PWb) and the same amplitude (|+A|=|−A|) for each of the pulse phases 30a and 30b. However, the pulse phases 30a and 30b may also be charged balance if the product of the amplitude and pulse widths of the two phases 30a and 30b are equal, as is known.

FIG. 3 shows that stimulation circuitry 28 can include passive recovery switches $41_i$, which are described further in U.S. Patent Application Publications 2018/0071527 and 2018/0140831. Passive recovery switches $41_i$ may be attached to each of the electrode nodes 39, and are used to passively recover any charge remaining on the DC-blocking capacitors Ci 38 after issuance of the second pulse phase 30b—i.e., to recover charge without actively driving a current using the DAC circuitry. Passive charge recovery can be prudent, because non-idealities in the stimulation circuitry 28 may lead to pulse phases 30a and 30b that are not perfectly charge balanced. Passive charge recovery typically occurs after actively-driven phases 30a and 30b have completed, and during at least a portion 30c (FIG. 2A) of the quiet periods between the pulses, by closing passive recovery switches $41_i$. As shown in FIG. 3, the other end of the switches $41_i$ not coupled to the electrode nodes 39 are connected to a common reference voltage $V_{CM}$. The common reference voltage $V_{CM}$ may be, for example VH/2 or may be another voltage, such as Vbat. As explained in the above-cited references, passive charge recovery tends to equilibrate the charge on the DC-blocking capacitors 38 and other capacitive elements by placing the capacitors in parallel between the reference voltage ($V_{CM}$) and the patient's tissue. Note that passive charge recovery is illustrated as small exponentially-decaying curves during 30c in FIG. 2A, which may be positive or negative depending on whether pulse phase 30a or 30b has a predominance of charge at a given electrode.

SUMMARY

Aspects of the disclosure relate to a stimulator device. According to some embodiments, the stimulator device comprises: a plurality of electrode nodes, each electrode node configured to be coupled to one of a plurality of electrodes configured to contact a patient's tissue; stimulation circuitry configured to provide actively-driven stimulation at at least one stimulation node selected from the plurality of the electrode nodes, wherein the stimulation comprises at least one pulse comprising at least a first phase; and passive charge recovery circuitry configured to provide passively-driven passive charge recovery for a passive charge recovery duration, wherein the passive charge recovery circuitry comprises a resistance circuitry configurable to adjust a recovery impedance during the passive charge recovery duration; and sensing circuitry configured to sense a neural response at at least one sensing node selected from the plurality of electrode nodes during the passive charge recovery duration. According to some embodiments, the resistance circuitry comprises a variable resistance circuitry. According to some embodiments, the variable resistance circuitry is configured to provide a first recovery impedance for a high-impedance portion of the passive charge recovery duration and a second recovery impedance for a low-impedance portion of the passive charge recovery duration, wherein the first recovery impedance is greater than the second recovery impedance. According to some embodiments, the sensing circuitry is configured to sense the neural response during the high-impedance portion of the passive charge recovery duration. According to some embodiments, the passive charge recovery circuitry comprises a plurality of switching circuits, wherein each of the plurality of switching circuits is coupled with a different one of the electrode nodes and is configured, when selected, to provide variable impedance between its respective electrode node and a common node. According to some embodiments, the common node comprises a reference voltage selected from the group consisting of a battery voltage, a compliance voltage, a fraction of a compliance voltage, and ground. According to some embodiments, each of the plurality of switching circuits comprises a plurality of switches wherein the switches are selectable to vary the resistance. According to some embodiments, the plurality of switches comprises a plurality of transistors in parallel. According to some embodiments, the stimulator device further comprises control circuitry configured with at least one algorithm, wherein the at least one algorithm is configured to determine a time at which the neural response will be present at the sensing electrode node and to time the passive charge recovery duration so that the high-impedance passive charge recovery portion will entirely overlap the time at which the neural response will be present the sensing electrode node. According to some embodiments, the stimulator device further comprises control circuitry configured with at least one algorithm, wherein the at least one algorithm is configured to determine when the neural response will be present at the sensing electrode node.

Also disclosed herein are methods for operating a stimulator device, the stimulator device comprising a plurality of electrode nodes, each electrode node configured to be coupled to one of a plurality of electrodes configured to contact a patient's tissue, the methods comprising: providing actively-driven stimulation at at least one stimulation node selected from the plurality of electrode nodes, wherein the stimulation comprises at least one pulse comprising at least a first phase; providing passively-driven passive charge recovery for a passive charge recovery duration, selecting at least one recovery impedance for the passive charge recovery duration, using a resistance circuitry of the stimulator device to provide the selected recovery impedance during the passive charge recovery duration, and sensing a neural response at at least one sensing electrode node selected from the plurality of electrode nodes during the passive charge recovery duration. According to some embodiments, the resistance circuitry comprises a variable resistance circuitry.

According to some embodiments, the selecting the least one recovery impedance comprises selecting a first recovery impedance for a high-impedance portion of the passive charge recovery duration and a second recovery impedance for a low-impedance portion of the passive charge recovery duration, wherein the first recovery impedance is greater than the second recovery impedance, and wherein sensing the neural response comprises sensing the neural response during the high-impedance portion of the passive charge recovery duration. According to some embodiments, the method further comprises determining a time at which the neural response will be present at the sensing electrode node and timing the passive charge recovery duration so that the high-impedance passive charge recovery portion will entirely overlap the time at which the neural response will be present the sensing electrode node. According to some embodiments, providing actively-driven stimulation comprises providing at least one first one or more pulses and at least one second one or more pulses. According to some embodiments, providing passively-driven passive charge recovery comprises proving a first passive charge recovery duration following each of the first one or more pulses and providing a second passive charge recovery duration following each of the second one or more pulses. According to some embodiments, selecting at least one recovery impedance comprises selecting a first recovery impedance for the first passive charge recovery duration and selecting a second recovery impedance for the second passive charge recovery duration, wherein the second recovery impedance is greater than the first recovery impedance. According to some embodiments, sensing the neural response comprises sensing the neural response during the second passive charge recovery duration.

Also disclosed herein is a stimulator device, comprising: a plurality of electrode nodes, each electrode node configured to be coupled to one of a plurality of electrodes configured to contact a patient's tissue; stimulation circuitry configured to provide actively-driven stimulation at at least one stimulation node selected from the plurality of the electrode nodes, wherein the stimulation comprises at least one pulse comprising at least a first phase; and passive charge recovery circuitry configured to provide passively-driven passive charge recovery for a passive charge recovery duration; and sensing circuitry configured to sense a neural response at at least one sensing node selected from the plurality of electrode nodes during the passive charge recovery duration. According to some embodiments, the neural response is created in response to the actively-driven stimulation. According to some embodiments, the passive charge recovery is configured to recover charge stored during the actively-driven stimulation. According to some embodiments, the passive charge recovery circuitry comprises a plurality of switching circuits, wherein each of the plurality of switching circuits is coupled with a different one of the electrode nodes and is configured, when selected, to provide variable resistance between its respective electrode node and a common node. According to some embodiments, the common node comprises a reference voltage selected from the group consisting of a battery voltage, a compliance voltage, a fraction of a compliance voltage, and ground. According to some embodiments, each of the plurality of switching circuits comprises a plurality of switches wherein the switches are selectable to vary the resistance. According to some embodiments, the plurality of switches comprises a plurality of transistors in parallel. According to some embodiments, the passive charge recovery duration comprises a high-impedance passive charge recovery duration and a low-impedance passive charge recovery duration, wherein: during the high-impedance passive charge recovery duration, the variable resistors are configured to provide passive charge recovery with a first impedance, and during the low-impedance passive charge recovery duration, the variable resistors are configured to provide passive charge recovery with a second impedance that is lower than the first impedance. According to some embodiments, the sensing circuitry is configured to sense the neural response during the high-impedance passive charge recovery duration. According to some embodiments, the stimulator device further comprises control circuitry configured with at least one algorithm, wherein the at least one algorithm is configured to determine a time at which the neural response will be present at the sensing electrode node and to time the passive charge recovery duration so that the high-impedance passive charge recovery duration will entirely overlap the time at which the neural response will be present the sensing electrode node. According to some embodiments, the stimulator device further comprises control circuitry configured with at least one algorithm, wherein the at least one algorithm is configured to determine when the neural response will be present at the sensing electrode node. According to some embodiments, the stimulation circuitry is further configured to provide actively-driven active charge recovery. According to some embodiments, the sensing circuitry comprises a differential amplifier, and wherein the differential amplifier receives the sensing electrode node at a first input, and wherein the differential amplifier receives a reference electrode node selected from one of the electrode nodes at a second input. According to some embodiments, each electrode node is coupled to its associated electrode through a DC-blocking capacitor. According to some embodiments, the stimulator device comprises an implantable pulse generator or an external trial stimulator.

Also disclosed herein is a method for operating a stimulator device, the stimulator device comprising a plurality of electrode nodes, each electrode node configured to be coupled to one of a plurality of electrodes configured to contact a patient's tissue, the method comprising: providing actively-driven stimulation at at least one stimulation node selected from the plurality of electrode nodes, wherein the stimulation comprises at least one pulse comprising at least a first phase; providing passively-driven passive charge recovery for a passive charge recovery duration, and during the passive charge recovery duration, sensing a neural response at at least one sensing electrode node selected from the plurality of electrode nodes. According to some embodiments, the neural response is present at the at least one sensing electrode node for a neural response duration and wherein the entire neural response duration of the neural response is sensed during the passive charge recovery. According to some embodiments, the method further comprises determining using control circuitry in the stimulator device when the neural response will be present at the sensing electrode node for the neural response duration. According to some embodiments, the passive charge recovery duration is timed such that the passive charge recovery duration will entirely overlap the neural response duration. According to some embodiments, providing passively-driven passive charge recovery for a passive charge recovery duration comprises: providing a high-impedance passive charge for a high-impedance passive charge recovery duration; and providing a low-impedance passive charge recovery for a low-impedance passive charge recovery duration. According to some embodiments, the neural response is sensed during the high-impedance passive charge recovery duration. According to some embodiments, the stimulator device comprises passive charge recovery circuitry configured to provide passively-driven passive charge recovery, wherein the passive charge recovery circuitry comprises a plurality of switching circuits, wherein each of the plurality of switching circuits is coupled with a different one of the electrode nodes and is configured, when selected, to provide variable resistance between its respective electrode node and a common node. According to some embodiments, during the high-impedance passive charge recovery duration, the switching circuits are configured to provide passive charge recovery with a first impedance, and during the low-impedance passive charge recovery duration, the switching circuits are configured to provide passive charge recovery with a second impedance that is lower than the first impedance. According to some embodiments, the method further comprises determining using control circuitry in the stimulator device when the neural response will be present at the sensing electrode node and timing the passive charge recovery duration so that the neural response is sensed during the high-impedance passive charge recovery duration. According to some embodiments, the method further comprising using the low-impedance passive charge recovery to recover stored charge not recovered by the high-impedance passive charge recovery.

BRIEF DESCRIPTION OF THE DRAWINGS

FIG. 1 shows an Implantable Pulse Generator (IPG), in accordance with the prior art.

FIGS. 2A and 2B show an example of stimulation pulses producible by the IPG, in accordance with the prior art.

FIGS. 5A and 5B show leads producing stimulation and show differential sensing of a neural response caused by the stimulation.

FIG. 6A shows a neural response as ideally sensed at a sensing electrode, while FIGS. 6B and 6C show how stimulation artifacts and passive charge recovery can interfere with sensing the neural response.

DETAILED DESCRIPTION

Figure 4:
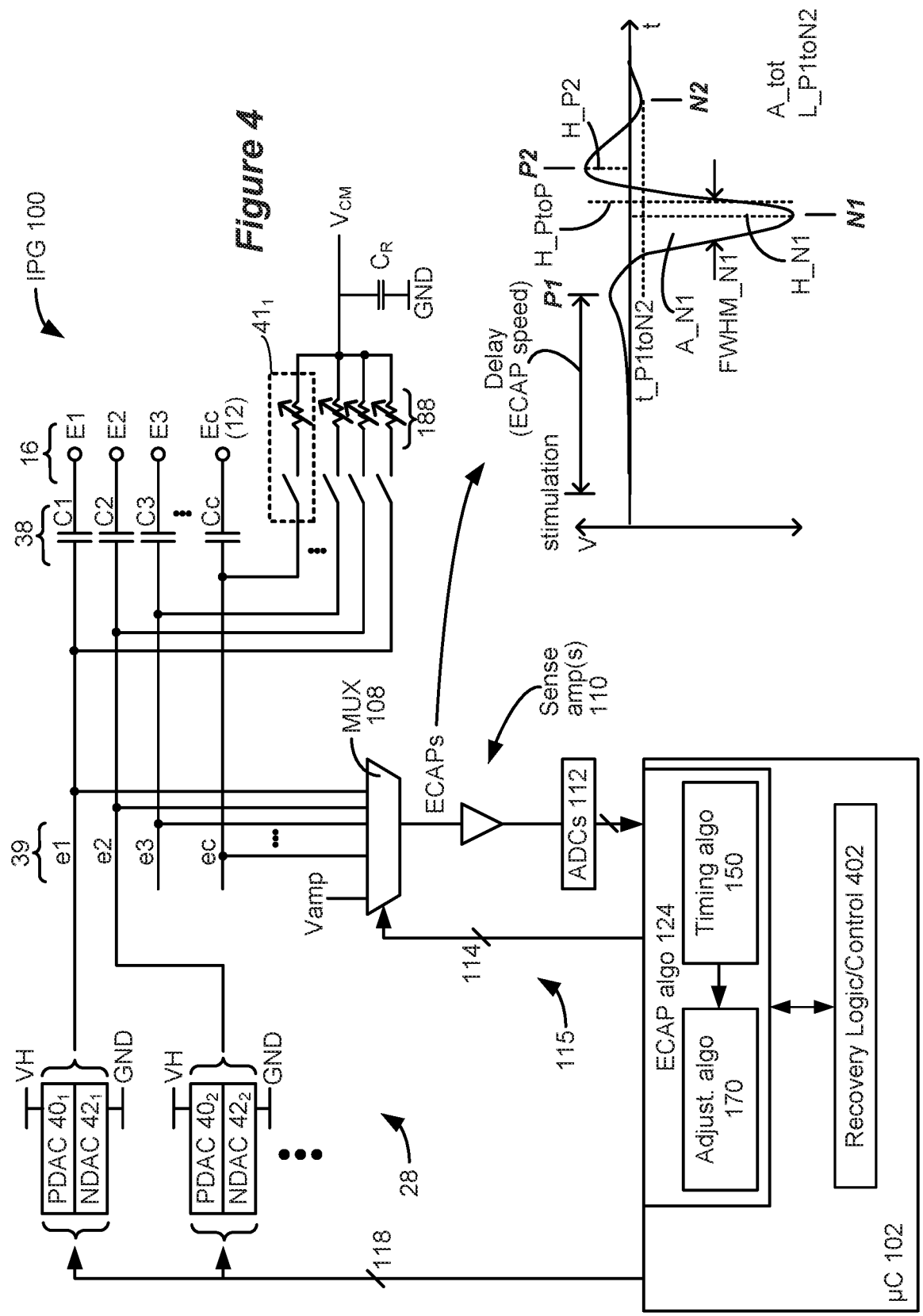
FIG. 4 shows an improved IPG having neural response sensing, and the ability to adjust stimulation dependent on such sensing.

An increasingly interesting development in pulse generator systems, and in Spinal Cord Stimulator (SCS) pulse generator systems specifically, is the addition of sensing capability to complement the stimulation that such systems provide. For example, and as explained in U.S. Patent Application Publication 2017/0296823, it can be beneficial to sense a neural response in neural tissue that has received stimulation from an SCS pulse generator. One such neural response is an Evoked Compound Action Potential (ECAP). An ECAP comprises a cumulative response provided by neural fibers that are recruited by the stimulation, and essentially comprises the sum of the action potentials of recruited fibers when they "fire." An ECAP is shown in FIG. 4, and comprises a number of peaks that are conventionally labeled with P for positive peaks and N for negative peaks, with P1 comprising a first positive peak, N1 a first negative peak, P2 a second positive peak and so on. Note that not all ECAPs will have the exact shape and number of peaks as illustrated in FIG. 4, because an ECAP's shape is a function of the number and types of neural fibers that are recruited and that are involved in its conduction. An ECAP is generally a small signal, and may have a peak-to-peak amplitude on the order of tens of microVolts to tens of milliVolts.

Also shown in FIG. 4 is circuitry for an IPG 100 that is capable of providing stimulation and sensing a resulting ECAP or other neural response or signal. The IPG 100 includes control circuitry 102, which may comprise a microcontroller for example such as Part Number MSP430, manufactured by Texas Instruments, which is described in data sheets at http://www.ti.com/lsds/ti/microcontroller/16-bit_msp430/overview.page?DCMP=MCU_other&HQS=msp430, which is incorporated herein by reference. Other types of controller circuitry may be used in lieu of a microcontroller as well, such as microprocessors, FPGAs, DSPs, or combinations of these, etc. Control circuitry 102 may also be formed in whole or in part in one or more Application Specific Integrated Circuits (ASICs), such as those described earlier. The disclosed circuitry and techniques can also be implemented in an ETS implantable stimulator, although this isn't further discussed.

Figure 3:
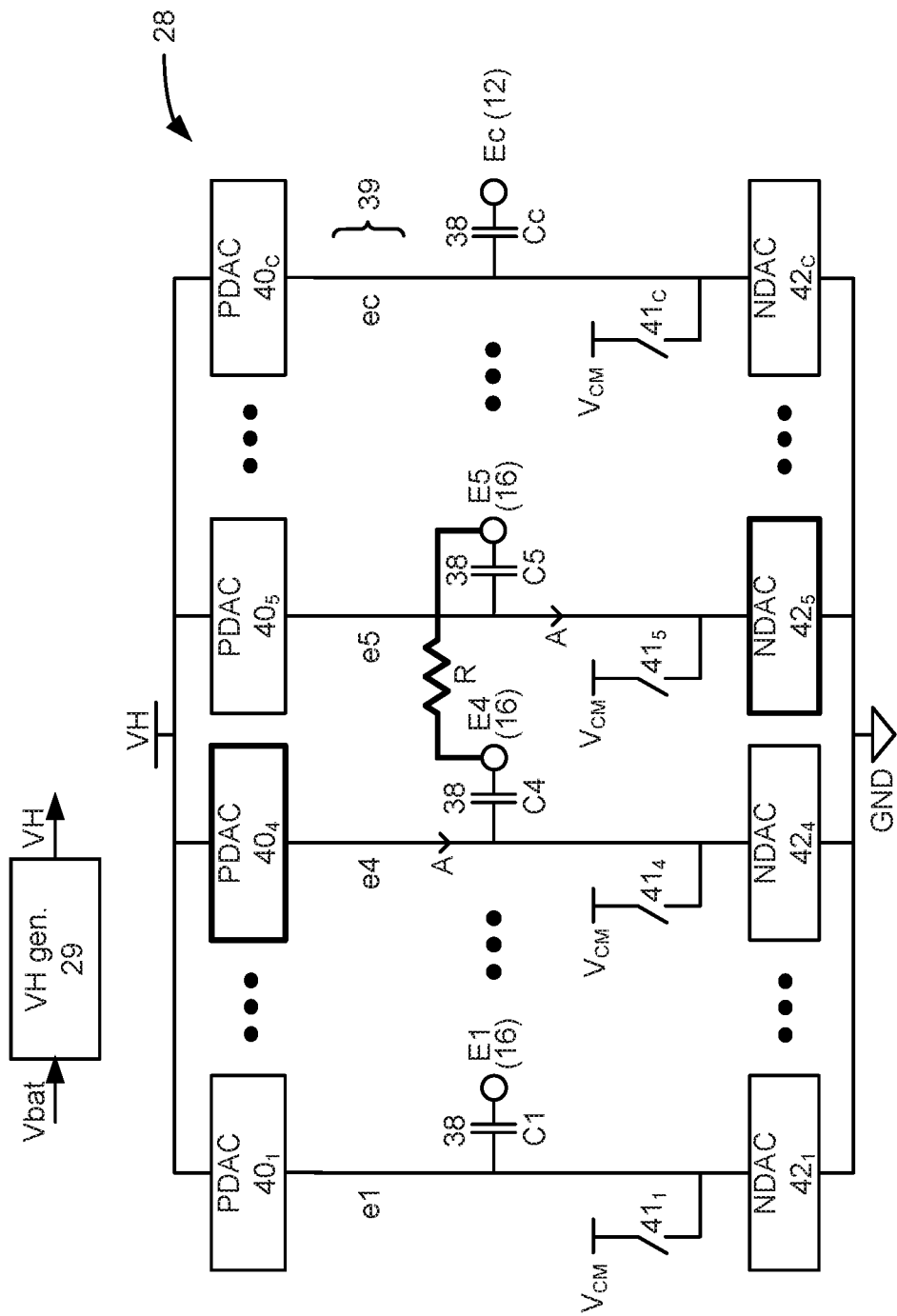
FIG. 3 shows stimulation circuitry useable in the IPG, in accordance with the prior art.

The IPG 100 also includes stimulation circuitry 28 to produce stimulation at the electrodes 16, which may comprise the stimulation circuitry 28 shown earlier (FIG. 3). A bus 118 provides digital control signals from the control circuitry 102 (and possibly from an ECAP algorithm 124, described below) to one or more PDACs $40_i$ or NDACs $42_i$ to produce currents or voltages of prescribed amplitudes (A) for the stimulation pulses, and with the correct timing (PW, f). As noted earlier, the DACs can be powered between a compliance voltage VH and ground. As also noted earlier, but not shown in FIG. 4, switch matrices could intervene between the PDACs and the electrode nodes 39, and between the NDACs and the electrode nodes, to route their outputs to one or more of the electrodes, including the conductive case electrode 12 (Ec). Control signals for switch matrices, if present, may also be carried by bus 118. Notice that the current paths to the electrodes 16 include the DC-blocking capacitors 38 described earlier, which provide safety by preventing the inadvertent supply of DC current to an electrode and to a patient's tissue. In the embodiment illustrated in FIG. 4, the passive charge recovery switches introduced earlier are replace by passive charge recovery switching circuits $41_i$. The passive charge recovery switching circuits serve to are used to passively recover any charge remaining on the DC-blocking capacitors by coupling the electrode nodes 39 to common reference voltage $V_{CM}$, as described above. The passive charge recovery switching circuits also serve to provide a variable resistance path between the electrode nodes 39 and $V_{CM}$. For ease of discussion, the passive charge recovery circuits are denoted as comprising variable resistors 188. The passive charge recovery switching circuits $41_i$ are described in more detail below, for example, with reference to FIG. 11. A capacitor CR may be provided between $V_{CM}$ and ground (GND) to lower the recovery impedance.

IPG 100 also includes sensing circuitry 115, and one or more of the electrodes 16 can be used to sense neural responses such as the ECAPs described earlier. In this regard, each electrode node 39 is further coupleable to a sense amp circuit 110. Under control by bus 114, a multiplexer 108 can select one or more electrodes to operate as sensing electrodes by coupling the electrode(s) to the sense amps circuit 110 at a given time, as explained further below. Although only one multiplexer 108 and sense amp circuit 110 is shown in FIG. 4, there could be more than one. For example, there can be four multiplexer 108/sense amp circuit 110 pairs each operable within one of four timing channels supported by the IPG 100 to provide stimulation. The analog waveform comprising the ECAP is preferably converted to digital signals by one or more Analog-to-Digital converters (ADC(s)) 112, which may sample the waveform at 50 kHz for example. The ADC(s) 112 may also reside within the control circuitry 102, particularly if the control circuitry 102 has A/D inputs. Multiplexer 108 can also provide a DC reference voltage, Vamp (e.g., GND), to the sense amp circuit 110, as is useful in a single-ended sensing mode.

So as not to bypass the safety provided by the DC-blocking capacitors 38, the input to the sense amp circuitry 110 is preferably taken from the electrode nodes 39, and so the DC-blocking capacitors 38 intervene between the electrodes 16 where the ECAPs are sensed and the electrode nodes 39. However, because the DC-blocking capacitors 38 will pass AC signals while blocking DC components, the AC ECAP signal will pass through the capacitors 38 and is still readily sensed by the sense amp circuit 110. In other examples, the ECAP may be sensed directly at the electrodes 16 without passage through intervening capacitors 38.

As shown, an ECAP algorithm 124 is programmed into the control circuitry 102 to receive and analyze the digitized ECAPs. One skilled in the art will understand that the ECAP algorithm 124 can comprise instructions that can be stored on non-transitory machine-readable media, such as magnetic, optical, or solid-state memories within the IPG 100 (e.g., stored in association with control circuitry 102).

In the example shown in FIG. 4, the ECAP algorithm 124 operates within the IPG 100 to determine one or more ECAP features, which may include but are not limited to:

- a height of any peak (e.g., H_N1) present in the ECAP;
- a peak-to-peak height between any two peaks (such as H_PtoP from N1 to P2);
- a ratio of peak heights (e.g., H_N1/H_P2);
- a peak width of any peak (e.g., the full width half maximum of a N1, FWHM_N1);
- an area under any peak (e.g., A_N1);
- a total area (A_tot) comprising the area under positive peaks with the area under negative peaks subtracted or added;
- a length of any portion of the curve of the ECAP (e.g., the length of the curve from P1 to N2, L_P1toN2) any time defining the duration of at least a portion of the ECAP (e.g., the time from P1 to N2, t_P1toN2);
- a time delay from stimulation to issuance of the ECAP, which is indicative of the neural conduction speed of the ECAP, which can be different in different types of neural tissues;

any mathematical combination or function of these variables (e.g., H_N1/FWHM_N1 would generally specify a quality factor of peak N1).

Once the ECAP algorithm 124 determines one or more of these features, it may then adjust the stimulation that the IPG 100 provides, for example by providing new data to the stimulation circuitry 28 via bus 118. This is explained further in U.S. Patent Application Publications 2017/0296823 and 2019/0099602, which are incorporated herein by reference in their entireties. In one simple example, the ECAP algorithm 124 can review the height of the ECAP (e.g., its peak-to-peak voltage), and in closed loop fashion adjust the amplitude of the stimulation current to try and maintain the ECAP to a desired value. The ECAP algorithm 124 can further include sub-algorithms, such as a timing algorithm 150 and an adjustment algorithm 170, which are described further below.

Embodiments of the microcontroller may comprise a Recovery Logic/Control block 402 that implements logic that issues a number of control signals that are used to control passive charge recovery, including control signals used to control the resistance at which passive charge recovery occurs. The details of recovery control and recovery logic for controlling the resistance at which passive charge recovery occurs is described in U.S. Patent Application Publication No. 2018/0071527, the entire contents of which are incorporated herein by reference. The Recovery Logic/Control block 402 can receive data from the timing algorithm 150 and/or the adjustment algorithm 170 for adjusting aspects of passive charge recovery, as described in more detail below.

FIGS. 5A and 5B show a percutaneous lead 15 (a paddle lead 19 or other lead could also be used), and show the stimulation program example of FIG. 2A in which electrodes E4 and E5 are used to produce biphasic pulses in a bipolar mode of stimulation, with (during the first phase 30a) E4 comprising an anode and E5 a cathode, although other electrode arrangements (e.g., tripoles, etc.) could be used as well. Such stimulation produces an electromagnetic (EM) field 130 in a volume of the patient's tissue around the selected electrodes. Some of the neural fibers within the EM field 130 will be recruited and fire, particularly those proximate to the cathodic electrode E5. Hopefully the sum of the neural fibers firing will mask signals indicative of pain in an SCS application, thus providing the desired therapy. The recruited neural fibers in sum produce an ECAP, which can travel both rostrally toward the brain and caudally away from the brain. The ECAP passes through the spinal cord by neural conduction with a speed which is dependent on the neural fibers involved in the conduction. In one example, the ECAP may move at a speed of about 5 cm/1 ms.

The ECAP is preferably sensed differentially using two electrodes, and FIGS. 5A and 5B show different examples. In FIG. 5A, a single electrode E8 on the lead 15 is used for sensing (S+), with another signal being used as a reference (S−). In this example, the sensing reference S− comprises a more distant electrode in the electrode array 17, or (as shown) the case electrode Ec. Reference S− could also comprise a fixed voltage provided by the IPG 100, such as ground or Vamp (FIG. 4), in which case sensing would be said to be single-ended instead of differential. In FIG. 5B, two lead-based electrodes are used for sensing, with such electrodes either being adjacent or at least relatively close to one another. Specifically, in this example, electrode E8 is again used for sensing (S+), with adjacent electrode E9 providing the reference (S−). This could also be flipped, with E8 providing the reference (S−) for sensing at electrode E9 (S+). Sensing a given ECAP at different electrodes can allow the ECAP algorithm 124 to understand the time difference between the arrival of the ECAP at each of the electrodes. If the distance x between the electrodes is known, the ECAP algorithm 124 can then compute speed of the ECAP. As noted above, ECAP speed is indicative of the neural fibers involved in neural recruitment and conduction, which can be interesting to know in its own right, and which may be useful to the ECAP algorithm 124 in adjusting the stimulation provided by the stimulation circuitry 28.

FIG. 6A shows an ECAP as ideally sensed at the sensing electrode S+(e.g., E8). In this example, it is assumed that sensing electrode E8 is at a distance d=12 mm away from the stimulation electrodes (e.g., E5), assuming the electrodes in the array are spaced at a distance x=4 mm apart. If one assumes that the ECAP travels at a speed of 50 mm/ms (again, this could vary depending on the neural tissue involved), the ECAP would start to pass the sensing electrode S+ at a time t1=0.24 ms. The ECAP itself is also spread in time ($t_{ECAP}$). This duration is again variable, but in FIG. 6A it is assumed that the ECAP is present at the sensing electrode S+ for one millisecond as a reasonable nominal value (i.e., $t_{ECAP}$=1 ms). Therefore, the ECAP will finish passing the sensing electrode S+ in this example at a time t2=t1+$t_{ECAP}$ (e.g., t2=1.24 ms). The time $t_{ECAP}$ that it takes the ECAP to pass the sensing electrode is referred to herein as the neural response duration.

FIG. 6B shows waveforms for the stimulation program, as well as the signals that would appear in the tissue at sensing electrode E8 (S+). As well as including the ECAP signal to be sensed (between times t1 and t2), the signal at the sensing electrode S+ also includes a stimulation artifact 134. The stimulation artifact 134 comprises a voltage that is formed in the tissue as a result of the stimulation, i.e., as result of the EM field 130 produced at stimulating electrodes E4 and E5. As described in U.S. Patent Application Publication 2019/02990069, which is incorporated herein by reference in its entirety, the PDACs and NDACs used to form the currents in the tissue have high output impedances. This can cause the voltage in the tissue to vary between ground and the compliance voltage VH used to power the DACs, which as noted earlier can be a high voltage (on the order of Volts). The magnitude of the stimulation artifact 134 at a given sensing electrode S+ or its reference S− can therefore be high (e.g., from milliVolts to Volts), and significantly higher than the magnitude of the ECAP. The magnitude of the stimulation artifact 134 at the sensing electrodes S+ and S− is dependent on many factors. For example, the stimulation artifact 134 will be larger if the sensing electrodes are closer to the stimulating electrodes (E4, E5). The stimulation artifact 134 is also generally larger during the provision of the pulses (during phases 30a and 30b), although it may still be present even after the pulse (i.e., the last phase 30b of the pulse) has ceased due to the capacitive nature of the tissue, which keeps the electric field 130 from dissipating immediately. As shown, the polarity of the stimulation artifact 134 varies between the phases 30a and 30b of the stimulation pulses when the current reverses polarity. Although the sensing artifact 134 and the ECAP are for simplicity shown separately in FIG. 6B, in reality they would superimpose (add) at the sensing electrode S+. Note that the magnitudes of the sensing artifact 134 and the ECAP are not necessarily drawn to scale; in particular, the sensing artifact 134 may be much larger.

The relatively large-signal background stimulation artifact 134 can make resolution and sensing of the small-signal ECAP difficult at the sense amp circuit 110. To ameliorate this concern, it can be beneficial to use a sensing electrode S+ that is far away from the stimulating electrodes. See, e.g., U.S. Patent Application Publication 2020/0155019, which is incorporated herein by reference in its entirety. This can be beneficial because the stimulation artifact 134 would be smaller at a more-distant sensing electrode, and because the ECAP would pass a distant sensing electrode at a later time when the stimulation artifact 134 might have dissipated. However, using a distant sensing electrode is not always possible or practical. For one, the electrode array 17 may simply not be large enough, and therefore no electrode may be suitably far enough away from the stimulating electrodes to ideally operate as the sensing electrode. Likewise, the magnitude of the ECAP also diminishes as distance from the stimulating electrodes increases, and therefore while the stimulation artifact 134 would be smaller at a more distant sensing electrode, so too would the ECAP, again making sensing difficult.

Assume then that E8 remains the sensing electrode in FIG. 6B. In this example, it is assumed that the pulses phases 30a and 30b have relatively long pulse widths, with both PWa of the first phase 30a and PWb of the second phase 30b equaling 0.25 ms. In sum, pulses are actively driven by the DAC circuitry (40/42) from 0 to 0.5 ms, and the stimulation artifact 134 is therefore predominant during the period. (This period may include an interphase period of short duration between phases 30a and 30b although for simplicity this isn't shown). Unfortunately, this stimulation artifact 134 overlaps in time with the ECAP at the sensing electrode S+, which again occurs between 0.24 (t1) and 1.24 ms (t2). This makes sensing of the ECAP difficult at the sensing electrode S+. First, the stimulation artifact 134 may be significantly larger than the small-signal ECAP. Further, the stimulation artifact 134 changes significantly during the time that the ECAP is present at the sensing electrode S+. In particular, at 0.25 ms, the stimulation artifact 134 changes polarity (from phases 30a to 30b), swinging from negative to positive values. Further, the stimulation artifact 134 falls from positive values to 0 at 0.5 ms (at the end of phase 30b), which in this example occurs in the middle of the ECAP. Because the ECAP is superimposed on the stimulation artifact 134, this makes resolution of the ECAP at the sense amp circuit 110 difficult.

FIG. 6C alleviates this sensing problem to some extent by making the pulse widths smaller. In this example, PWa and PWb have been reduced to 0.12 ms each. As such, the stimulation artifact 134 largely ends at 0.24 ms (at the end of phase 30b) when the ECAP first starts to appear at the sensing electrode S+(at t1). As such, the ECAP and stimulation artifact 134 do not significantly overlap at the sense electrode S+, and this is further true if the pulse widths are reduced further. However, this solution may not be ideal. First, adjusting the pulse widths may simply not be possible, as they may not be what is needed to provide adequate stimulation therapy for the patient. Also, simply reducing the pulse widths to avoid overlap with the ECAP may not be possible if the ECAP travels relatively fast.

Furthermore, although the ECAP may no longer overlap significantly with the stimulation artifact 134 in FIG. 6C, the ECAP does still overlap during a period 30c where it may be desirable to provide passive charge recovery after the active pulse phases 30a and 30b have completed. As noted earlier, passive charge recovery involving closing passive charge recovery switching circuits 41$_i$ (FIG. 4), which connects the electrode nodes ei 39 to the reference potential (such as $V_{CM}$). Even if the switching circuit 418 at sensing electrode E8 is not closed, the effect of closing some of the switches will cause a current to passively flow in the tissue, which also causes a variable voltage artifact in the tissue as well (not shown). See, e.g., U.S. Patent Application Publication 2018/0140831. In short, passive charge recovery makes sensing of the ECAP difficult as it—like the stimulation artifact 134—can create a time varying voltage in the tissue that is significantly larger than the ECAP. Note that the provision of passive recovery 30c in FIG. 6B is also problematic, because there as well the passive charge recovery period 30c again overlaps in time with the ECAP to some extent.

Figure 7:
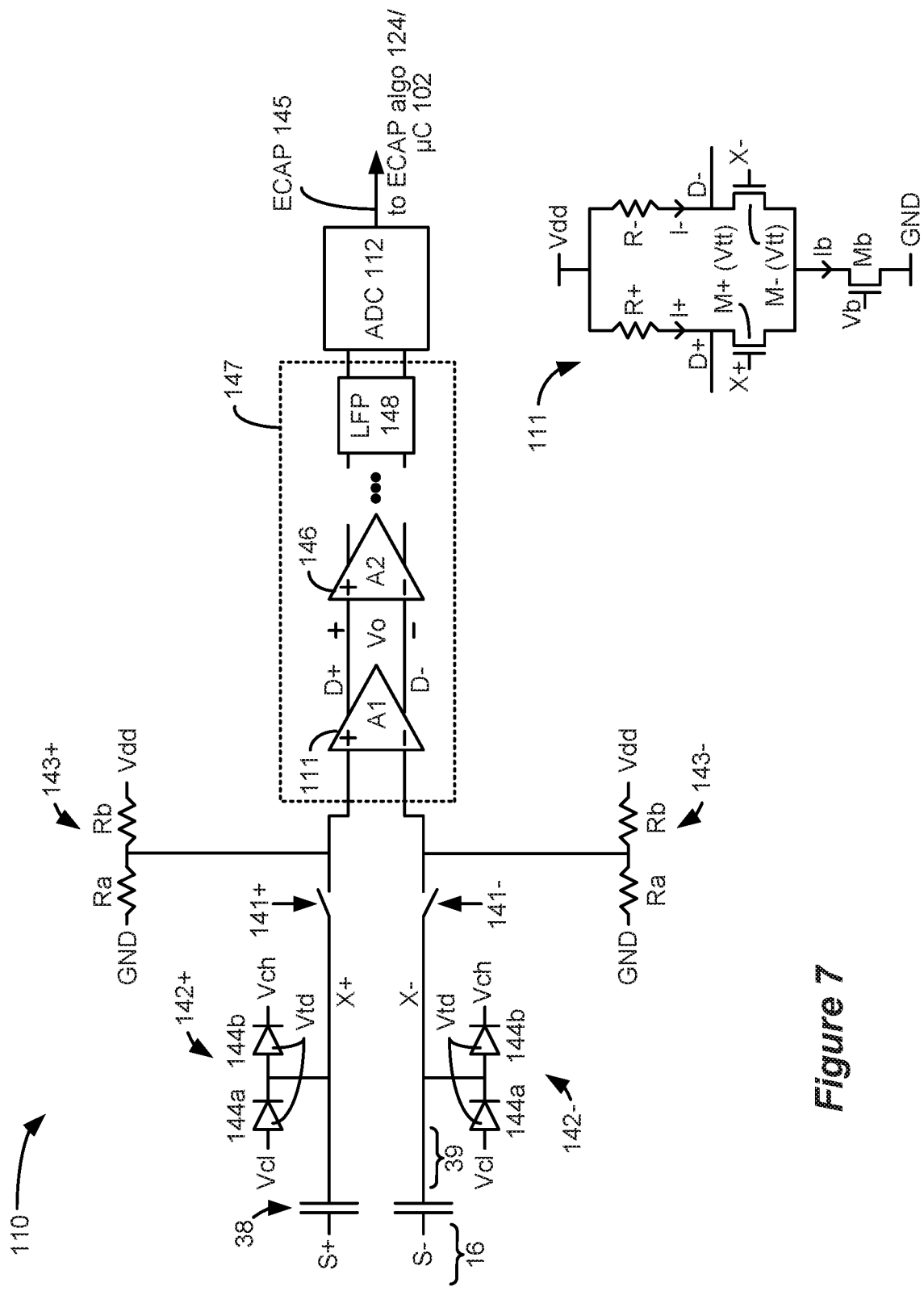
FIG. 7 shows sense amp circuitry useable to sense the neural response.

As noted earlier, an ECAP is preferably sensed differentially using electrodes S+ and S−, which are both exposed to the tissue, therefore allowing the artifacts in the tissue (i.e., stimulation artifacts 134 or artifacts related to passive charge recovery) to be subtracted from the ECAP measurement to at least some degree. A sense amp circuit 110 that provides differential sensing is shown in FIG. 7. The sense amp circuit 110 includes a differential amplifier 111. Also shown is an example of the circuitry within the differential amplifier 111, although it should be noted that many different differential amplifier circuits exist and can be used in sense amp circuit 110 as well. Sensing electrode S+ and sensing reference electrode S− are coupled through the DC-blocking capacitors 38 (if used) to derive signals X+ and X− at the electrode nodes 39 that are presented to the positive and negative inputs of the differential amplifier 111. Signals X+ and X− will be largely the same as S+ and S− present at the selected sensing electrodes, but with DC signal components removed. X+ and X− are provided to the gates (control terminals) of transistors M+ and M− in the differential amplifier 111. The drains of the transistors M+ and M− are connected to differential outputs D+ and D−, which in turn are coupled to the amplifier's power supply voltage Vdd via resistances R+ and R−. The sources of the transistors M+ and M− are connected to ground as the other power supply voltage through a common bias transistor Mb, which sets the total current Ib that, in sum, can pass through each of the legs (I+, I−) of the differential amplifier. Resistances R+ and R− are equal and are represented as simple resistors, although active devices (e.g., PMOS transistors) could also be used. The output of the amplifier 111, Vo, equals the difference in the voltages at outputs D+ and D−, which in turn is influenced by the difference in the signals present at X+ and X−. Signals X+ and X−, if different (e.g., if an ECAP is present at S+), will turn transistors M+ and M− on to different degrees, thus causing different currents I+ and I− to flow through each leg. This produces different voltage drops across the resistances R+ and R−, and thus different voltages at D+ and D−. In short, Vo=D+−D−=A1(X+−X−), where A1 is the gain of the amplifier 111.

The differential amplifier 111 may provide its output to various processing circuits 147 prior to presentation to the control circuitry 102 and the ECAP algorithm 124. For example, the differential amplifier 111's differential output Vo may be provided to the inputs of another differential amplifier 146, and to still further differential amplifiers in series, etc. This can be helpful in increasing the gain of the detected ECAP signal, because the gains of each amplifier stage will multiply (A1*A2, etc.). A follower circuit or buffer could also be used in series as part of the processing circuitry 147 between the differential amplifier 111 and the ADC 112 but such stages are not shown. Further, the processing circuitry 147 may include a Low Pass Filter (LPF) 148 to remove high-frequency components in the ECAP signal that are not of interest, or that are inconsistent with the rate at which the ADC 112 will sample the signal.

In one example, the LFP 148 removes frequency components of 25 kHz or higher. Processing circuitry 147 may comprise part of the control circuitry 102.

To prevent damage to or improper operation of the differential amplifier 111 (i.e., the first differential amplifier in series), inputs X+ and X− may be provided with clamping circuits 142+ and 142− respectively. In the example shown, clamping circuit 142+ comprises a serial connection of diodes 144a and 144b which are forward biased between a low clamp reference voltage reference (Vcl) and a high clamp reference voltage (Vch), and with signal X+ connected to a node between the diodes. Vcl and Vch preferably comprise ground and the power supply voltage Vdd (e.g., 3.3V). In this example, it is assumed that the diodes 144a and 114b have a forward biased threshold voltage (Vtd) of 0.6V. Diode 144a would conduct (turn on) if the voltage at X+ is less than −0.6 Volts. Because such conductance is of very low resistance, X+ is effectively clamped to a minimum of Vmin=−0.6 Volts. If it is assumed that Vdd=3.3 V, diode 144b would conduct if X+ is greater than 3.9V Volts, which would clamp X+ to a maximum of Vmax=3.9V. If the voltage at X+ is at or between −0.6 and 3.9 Volts, neither diode 144a nor 144b in clamping circuit 142+ would conduct. Clamping circuit 142− is similar, but connects to signal X−, and so similarly clamps X− to a voltage at or between −0.6 and 3.9 Volts. Modifications may be made to the clamping circuits 142+ and 142− to adjust the window of permissible voltages at which clamping does not occur. For example, Vcl and Vch could be generated by their own generator circuits to produce unique values different from ground and Vdd; different numbers of diode could be used; Zener diodes could be used that break down and thus clamp X+ or X− at specified reverse bias voltages; etc.

Also shown in FIG. 7 are blanking switches 141+ and 141− which are respectively used to pass signals at X+ and X− to the differential amplifier. Blanking switches 141+ and 141− can be used to protect the differential amplifier 111, and specifically to protect the amplifier 111 from receiving voltages that are too high at signals X+ and X−. (Note however the clamping circuits 142+ and 142−, which limit the voltages at X+ and X−, may alleviate the need for blanking switches 141+ and 141− to some degree). Blanking switches can be used in conjunction with the disclosed technique, as described further below. Note that blanking switches 141+ and 141− can comprise logic switches used to route the electrode nodes 39 to the sense amp circuit 110. For example, blanking switches 141+ and 141− can comprise switches within the multiplexer 108 (FIG. 4), or they may comprise independent switches.

The sense amp circuit 110 may further include DC-level shifting circuits 143+ and 143− to set signals X+ and X− to a DC voltage reference consistent with the input requirements for the differential amplifier 111. The differential amplifier 111 can only operate reliably if signals X+ and X− are of a magnitude that causes current I+ and I− to flow in each leg of the amplifier. In this regard, to sense the small-signal ECAP, X+ and X− should be higher than the threshold voltage of the amplifier's input transistors M+ and M− (e.g., greater than Vtt=0.7 V). It is further preferred that X+ and X− not exceed the power supply voltage Vdd of the differential amplifier (e.g., Vdd=3.3V) for proper amplifier operation. Accordingly, signals provided to the differential amplifier 111 are preferably referenced with respect to a DC voltage reference within this operating range. This reference could comprise ½Vdd (e.g., 1.65 V), which comprises a midpoint between Vdd and ground. More preferably, the DC voltage reference could comprise ½(Vdd−Vtt)+Vtt (e.g., 2.0 V), as this value would be midpoint within the operating range 0.7V and 3.3V, and thus allow X+ and X− to symmetrically swing +/−1.3V from the reference while still providing an input magnitude suitable to operate the differential amplifier 111. While such circuits can take different forms, in the example shown the DC-level shifting circuits 143+ and 143− comprise resistor ladders, comprising resistors Ra and Rb in series biased between Vdd and ground, with signals X+ and X− connected to nodes between the resistors. This sets the DC voltage reference of both X+ and X− to Ra/(Ra+Rb)*(Vdd−ground). Thus, by setting the values of Ra and Rb appropriately, the DC voltage reference can be set to any desired value between Vdd and ground, such as 2.0 V. AC signals then coupling to X+ and X− through the capacitors 38 (such as the ECAP and/or the stimulation artifact 134) will then be referenced to (and ride on top of) this DC voltage reference. As a general matter, this allows the differential amplifier 111 to be affected by the ECAP at X+, because the superposition of the ECAP and the DC voltage reference will cause a change in current I+. Preferably, Ra and Rb are large resistances, such 1 Mega-Ohm or higher.

Because the stimulation artifact 134 is present at both the sensing electrode S+ and reference electrode S−, the differential amplifier 111 will ideally subtract artifacts in the tissue (i.e., stimulation artifact 134 and artifacts related to passive charge recovery) as a common mode voltage from the output (Vo), leaving only the ECAP to be sensed. However, the magnitude of such artifacts may not be exactly the same at sensing electrodes S+ and S−, which is not surprising as each is necessarily located at a different distance from the stimulating electrodes. Thus, common mode removal of such artifacts by the differential amplifier 111 may be not be perfect. Furthermore, it is difficult to design the differential amplifier 111 to resolve the ECAP when the artifacts are both relatively large and varying over time. This is a particular problem in the scenarios discussed earlier with reference to FIGS. 6B and 6C, where the ECAP overlaps in time at the sensing electrode S+ with the stimulation artifact 134 and passive recovery artifacts to significant degrees.

Conventional wisdom, as described earlier, teaches that it is not desirable to sense an ECAP during the provision of pulses to the tissue. Again, this is because a stimulation artifact—as caused by active stimulation or passive charge recovery that may follow—may be large or changing during such periods. However, contrary to this conventional wisdom, the inventors have devised new ECAP sensing strategies, which are capable of sensing the ECAP during the active and/or passive charge recovery phases. U.S. Patent Application Publication 2020/0305745, the entire contents of which are incorporated herein by reference, describes ECAP sensing strategies for sensing ECAPs during the provision of active stimulation/active charge recovery. The instant disclosure describes ECAP sensing during passive charge recovery.

Figure 8:
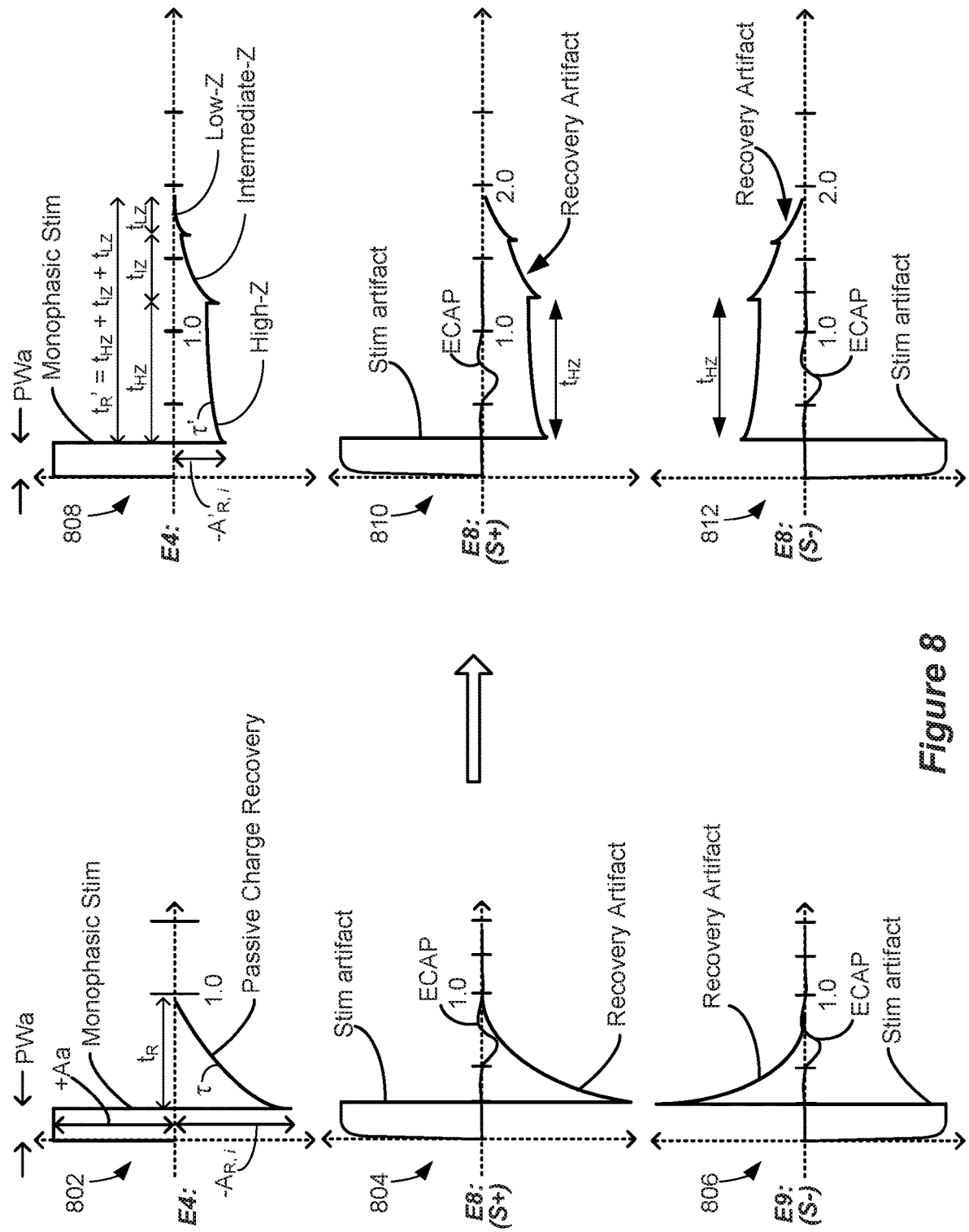
FIG. 8 shows stimulation and passive charge recovery, including sensing of neural response during passive charge recovery.

FIG. 8 illustrates the waveform of a monophasic pulse 802 delivered at electrode E4. Passive charge recovery is used to recover charge following the pulse. Note that in FIG. 8, while the waveform of only the single stimulation electrode E4 is illustrated, it is understood that another electrode, such as one of the other lead electrodes or the case electrode is serving as a counter electrode. Note also, that while a simple monophasic pulse is illustrated for clarity in FIG. 8, passive charge recovery may also be used in conjunction with bi-phasic pulses, as well as with other more complex waveforms. The ECAP strategies described herein may be used with any stimulation waveform that includes passive charge recovery.

The monophasic waveform 802 comprises a monophasic stimulation pulse having an amplitude of +Aa and is followed by a passive charge recovery phase. The passive charge recovery phase has an initial amplitude of $-A_{R,i}$, which is essentially equal to the voltage buildup of the blocking capacitors $V_C$ divided by the tissue impedance $R_t$. In other words, $-A_{R,i} \approx V_C/R_t$.

The amplitude of the passive charge recovery phase decays exponentially over a time period $t_R$ according to a time constant $\tau$ which is equal to the capacitance of the capacitors multiplied by the tissue impedance $R_t$. The time period tR to recover essentially all of the charge is approximately $5\tau$. As explained further below, the shape of the decay curve of the passive charge recovery can be controlled/altered by including variable or selectable resistors in series with the passive charge recovery switches 41 (see, e.g., FIGS. 3 and 4).

Still referring FIG. 8, the signals 804 and 806 appearing in the tissue at the sensing electrodes (E8 and E9) are also illustrated. The signals 804 and 806 include a stimulation artifact comprising a voltage formed in the tissue as a result of the stimulation, i.e., as a result of the EM field produced at the stimulation electrode E4. The signals 804 and 806 also include a recovery artifact comprising a voltage that is formed in the tissue as a result of the passive charge recovery. Like the passive charge recovery of the stimulation waveform 802, the recovery artifact of the signals 804 and 806 are each represented as exponentially-decaying curves. The time constants of the recovery artifact signals are each a function of the time constant of the passive charge recovery portion of the stimulation waveform 802, from which the artifacts are generated. In other words, changes in the passive charge recovery of the stimulation waveform 802 will be reflected in the artifact signals 804 and 806.

It is apparent from FIG. 8 that if the ECAP signal to be sensed at the sensing electrodes overlaps with the recovery artifact at those electrodes, sensing of the ECAP signal will be difficult for the same reasons described above with respect to sensing an ECAP signal that overlaps with actively driven charge recovery. The inventors have discovered that ECAP signals that overlap with the recovery artifact can be better resolved by implementing a high-impedance passive charge recovery. For example, a high recovery impedance can be used during the initial passive recovery phase during the time at which the ECAP signal is expected at the sensing electrodes. The impedances of passive charge recovery phase can be controlled by including variable or selectable resistors in the passive charge recovery switching circuitry, as explained in more detail below.

Waveform 808 of FIG. 8 is a monophasic stimulation pulse followed by a multistep passive charge recovery. The multistep passive charge recovery comprises a high-impedance (Z) duration, an intermediate-impedance duration, and a low-impedance duration. The initial high-impedance phase has an initial amplitude $-A'_{R,i}$, which is lower in magnitude than $-A_{R,i}$ (of waveform 802), because now the initial amplitude is essentially equal to $V_C/(R_t+R_R)$, where $R_R$ is the added recovery impedance.

The high-impedance passive charge recovery decays according to a time constant $\tau'$, which is a function of the tissue resistance $R_t$ plus the added recovery resistance $R_R$, (i.e., $\tau'$ is a product of the capacitance times the sum of $R_t$ and $R_R$). The duration of the high-impedance phase is denoted as $t_{HZ}$ and can be controlled by the system. Note that during the high-impedance passive charge recovery the system is near-steady state, i.e., the passive recovery current is slowly decaying and the decay curve is relatively flat. Note also that during the high-impedance duration, all of the charge may not be recovered, i.e., the decay curve may not decay completely to the baseline. Thus, following the high-impedance duration, charge balance can be attained by using a lower impedance passive charge recovery for more aggressive (i.e., fast) charge recovery. The waveform 808 includes an intermediate-impedance duration, which is implemented for a time period $t_{IZ}$, and low-impedance duration, which is implemented for a time period $t_{LZ}$. Note that the intermediate-impedance and the low impedance recoveries have time constants $\tau''$, and $\tau'''$ respectively (thought not indicated in the Figure). The total passive charge recovery duration $t_R'$, is the sum of the durations of the high-, intermediate-, and low-impedance phases. It should be noted that the number of different impedance phases included during the charge recovery may be more or fewer than three (which is shown simply for the purposes of illustration). According to some embodiments, the impedance during the high-impedance phase may be on the order of 10 kΩ; the intermediate-impedance phase may be 300-1800Ω, and the low impedance phase may be 50-100Ω. These values are exemplary only; other impedances may be used.

The benefit of using a high-impedance passive charge recovery during the time at which the ECAP is expected to be present at the sensing electrodes is illustrated in the signals 810 and 812 sensed at the sensing electrodes. As illustrated, the time period of the passive charge recovery is lengthened and time period of the high-impedance duration $t_{HZ}$ entirely overlaps the ECAP (i.e., the neural response duration) at the sensing electrode. This benefits ECAP sensing in a few ways. First, although the recovery artifact is still present when the ECAP is present at the sensing electrodes, this artifact is smaller, because magnitude of the artifact has been reduced. This assists sensing by the differential amplifier 111 (FIG. 7), as the differential amplifier can more easily process (i.e., subtract out) a smaller common mode voltage that is closer to being on par with the magnitude of the ECAP.

Second, by extending the duration of the passive charge recovery phase, this phase no longer starts or ends during (in the middle of) the ECAP at the sensing electrodes. This also eases sensing because the recovery artifact is relatively constant (i.e., flat) during the ECAP at the sensing electrodes.

Also, it should be noted, stimulation therapy to the patient is not significantly altered. The monophasic stimulation pulse (or the first phase of a biphasic pulse) creates significant therapeutic effect in the patient, and thus the amplitude Aa and pulse width PWa are generally tailored for the patient. In this example, these pulse parameters Aa are PWa not altered. The passive charge recovery phase is generally not therapeutically significant and thus can be changed without significant impact to the patient.

Note that there can be practical limits to the solution of FIG. 8. For example, if the pulses are of high frequency F, there may not be sufficient time between subsequent pulses to fit an extended passive charge recovery. However, this problem can simply be mitigated by not providing a subsequent pulse until after ECAP measurement has completed. This should not be significantly problematic to patient therapy, as ECAP measurements would normally not be taken after each pulse, but instead only need to be taken occasionally; occasionally delaying or missing a therapeutic pulse will not significantly affect stimulation therapy.

In the disclosed technique, as shown in FIG. 8, blanking should not occur during the passive charge recovery phase when the ECAP is sensed. That is, switches such as 141+ and 141− (FIG. 7) to the inputs of the differential amplifier 111 should be closed to allow sensed signals S+ and S− (and X+ and X−) to reach the inputs to the amplifier. During stimulation phase, blanking can occur—i.e., switches 141+ and 141− can be opened. This can help protect the differential amplifier 111 from saturating, which may occur if the stimulation artifact is large during the stimulation phase. That being said, it is not strictly necessary to blank during the stimulation phase, particularly if clamping circuits 142+ and 142− are used to limit the voltages on X+ and X−.

To implement high-impedance passive charge recovery to assist sensing a neural response, several timing aspects need to be considered. First, it is generally desirable (though not always necessary) that all of the charge stored on the DC blocking capacitors during the actively driven stimulation be recovered during the stimulation period. In other words, if all of the charge is not recovered during the period, then charge may continue to build up on the capacitors over a number of periods. Also, it is generally desirable that the neural response be sensed during the high-impedance duration and that the high-impedance duration completely overlap with the neural response duration. Thus, according to embodiments of the disclosed neural sensing strategy, the charge recovery is provided and timed so that the neural response is sensed during high-impedance passive charge recovery phase and additional charge recovery (either passively-driven passive charge recovery of lower impedance and/or actively-driven active charge recovery) is provided to recover any additional remaining charge.

Figure 9:
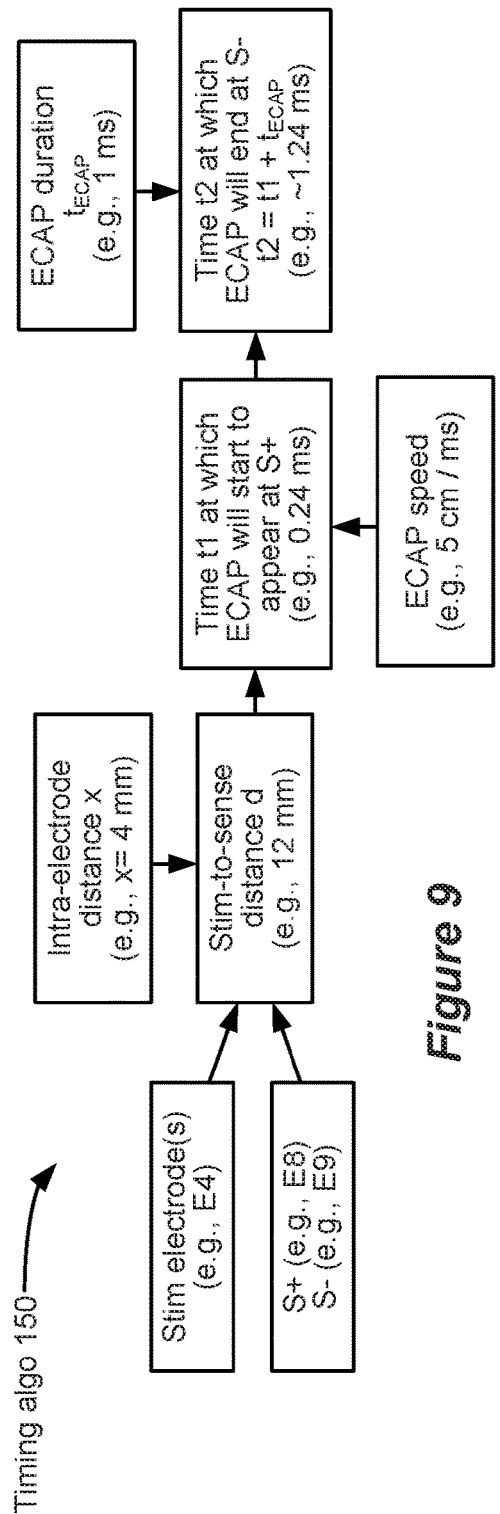
FIG. 9 shows a timing algorithm operable to determine when a neural response starts and stops at a sensing electrode.
Figure 10:
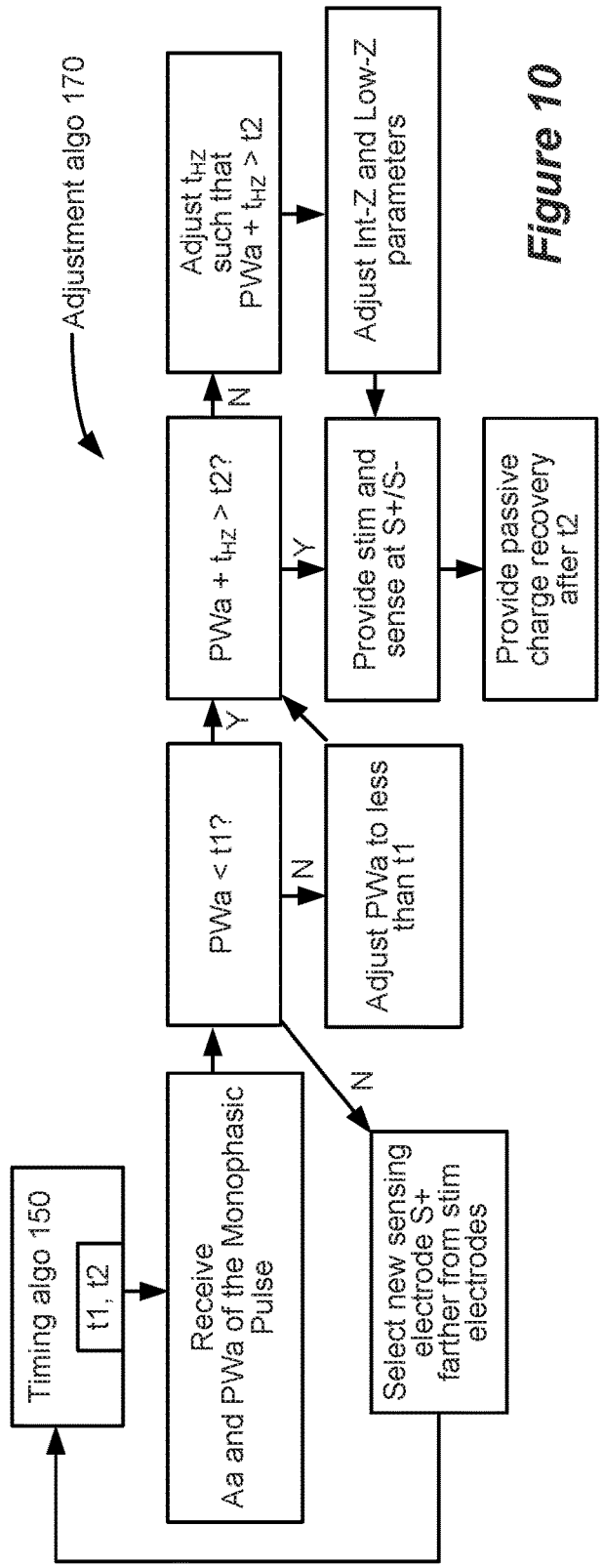
FIG. 10 shows an adjustment algorithm useable in conjunction with the timing algorithm to ensure that a high-impedance passive charge recovery duration will overlap a neural response at a sensing electrode.

FIGS. 9 and 10 disclose optional algorithms 150, and 170 that can be used to adjust the passive charge recovery to assist with ECAP sensing. FIG. 9 discloses a timing algorithm 150 which determines when an ECAP will start (t1) and finish (t2) (see FIG. 6A) appearing at sensing electrodes S+ and S− that have been chosen for ECAP sensing. In other words, the algorithm determines the neural response duration. The timing algorithm 150 can receive as inputs, or be programmed with, the selected sensing electrode(s) (e.g., S+=E8; S−=E9) and stimulating electrode(s) (e.g., E4), and the distance (x) between electrodes in the electrode array (e.g., 4 mm). From this, the algorithm 150 can compute the distance (d) between the stimulation and sensing electrodes (e.g., 12 mm). The timing algorithm 150 can also receive, or be programmed with, an expected ECAP speed (e.g., 5 cm/ms). Note that this speed can be an estimated speed, or a speed that is actually measured by the IPG. From distance d and the ECAP speed, a time t1 at which the ECAP will first appear at the sensing electrode can be determined (e.g., d/speed=0.24 ms). The timing algorithm 150 can also receive, or be programmed with, an expected ECAP duration ($t_{ECAP}$=1 ms). Again, this value can also be measured in the IPG. This allows a time t2 at which the ECAP will finish appearing at the electrode to be computed (e.g., t2=t1+$t_{ECAP}$). If necessary, t1 and t2 can also be adjusted to provide additional margin—e.g., t1 can be slightly lowered and t2 can be slightly increased to ensure that t1 and t2 are suitable for detecting the ECAP (using adjustment algorithm 170 which follows).

Although not shown, timing algorithm 150 may also determine t1 and t2 using measurements alone. For example, short test pulses of low pulse widths can be used which are unlikely to produce significant artifacts, with the resulting ECAP measured by the sense amp circuitry 110. Thus, t1 and t2 may be determined empirically.

Once t1 and t2—the start and finish of the ECAP at the sensing electrode(s) S+/S− have been determined using timing algorithm 150, an adjustment algorithm 170 may use these values to determine how to adjust a prescribed pulse and passive charge recovery, as shown in FIG. 10. In particular, adjustment algorithm 170 can adjust the passive charge recovery to ensure that the high-impedance duration of the passive charge recovery is long enough to overlap with the ECAP at the sensing electrodes S+/S−. In this regard, pulse parameters for a prescribed pulse—presumably a pulse determined to provide adequate patient therapy—are received, which in this example comprises parameters for a monophasic pulse having an amplitude Aa and a pulse width PWa. As noted above, though monophasic pulses are used as examples for reasons of simplicity, the methods described herein can be used with pulses of any shape.

The adjustment algorithm 170 as first step can, optionally, assess the timing of the pulse phase (PWa) to determine whether it is smaller than t1. As discussed earlier with regard to FIGS. 6B and 6C, if PWa is not smaller than t1, this can be problematic to ECAP sensing, because the ECAP would be present at the sensing electrode S+ when the stimulation artifact 134 is changing (e.g., between phases 30a and 30b or between 30 a and passive charge recovery). If PWa is not less than t1, the adjustment algorithm 170 could take certain actions, such as adjusting PWa to make it less than t1 (even though this could change the therapy provided by first phase 30a), or choosing anew sensing electrode(s) S+/S− that might be further away from the stimulating electrodes. This step may not be necessary if it is known a priori that PWa<t1, and therefore that the ECAP should not overlap with the first phase 30a of the pulse. Note that choosing new sensing electrodes would change the timing t1 and t2 at which the ECAP would start and finish at that new sensing electrode, and therefore the newly chosen sensing electrode(s) S+/S− can be passed back to the timing algorithm 150 (FIG. 9) so that t1 and t2 can be re-determined, and adjustment algorithm 170 repeated.

If PWa<t1, the adjustment algorithm 170 can continue by assessing whether the duration of both active pulse phase and the high-impedance charge recovery phase is less than t2, i.e., if PWa+$t_{HZ}$>t2. If this is true, then the ECAP at the sensing electrode(s) should fall entirely within the high-impedance charge recovery phase, as is desired. In this case, the IPG can simply provide the stimulation, and sense the ECAP during the high-impedance phase, similarly to what was shown in FIG. 8.

If PWa+$t_{HZ}$ is not greater than t2, this means that the high-impedance passive charge recovery phase ends somewhere in the middle of when the ECAP is expected to be present at the sensing electrode(s). In other words, the high-impedance duration does not completely overlap the neural response duration. The adjustment algorithm 170 can thus adjust the timing of the high-impedance passive charge recovery duration by increasing $t_{HZ}$ so that PWa+$t_{HZ}$ is now greater than t2. At this point, the ECAP at the sensing electrode should fall entirely within the high-impedance passive charge recovery duration.

According to some embodiments, the adjustment algorithm 170 may also check to confirm that the passive charge recovery parameters allow for complete charge recovery during the pulse cycle, i.e., before the next stimulation pulse. The adjustment algorithm may adjust the timing and/or resistance used during the intermediate-impedance and/or low-impedance phases of the passive charge recovery. For example, if the high-impedance passive charge recovery is long, then the intermediate and/or low impedance phases might be applied more aggressively (i.e., with lower impedances) to ensure that complete charge recovery occurs before the following stimulation pulse is issued. After this adjustment to the passive charge recovery phase is made, the IPG can provide the stimulation, and sense the ECAP during the adjusted high-impedance passive charge recovery duration.

Although algorithms 150 and 170 are described as separate for ease of illustration, they could be combined into a single algorithm.

As shown in FIG. 4, the timing and adjustment algorithms can comprise part of the ECAP algorithm 124 operable in the control circuitry 102 (FIG. 4). As mentioned above, the timing and adjustment algorithms may provide data to recovery logic/control 402, which issues control signals to the passive charge recovery circuitry to implement the prescribed impedance and timing adjustments to the passive charge recovery phase. The impedance of the passive charge recovery phases is adjusted using variable resistors 188 (i.e., adjusted using the variable resistance of the passive charge recovery switching circuitry 41, FIG. 4). Thus, the recovery switching circuitry 41 may be considered as an example of resistance circuitry for controlling the recovery impedance.

Figure 11:
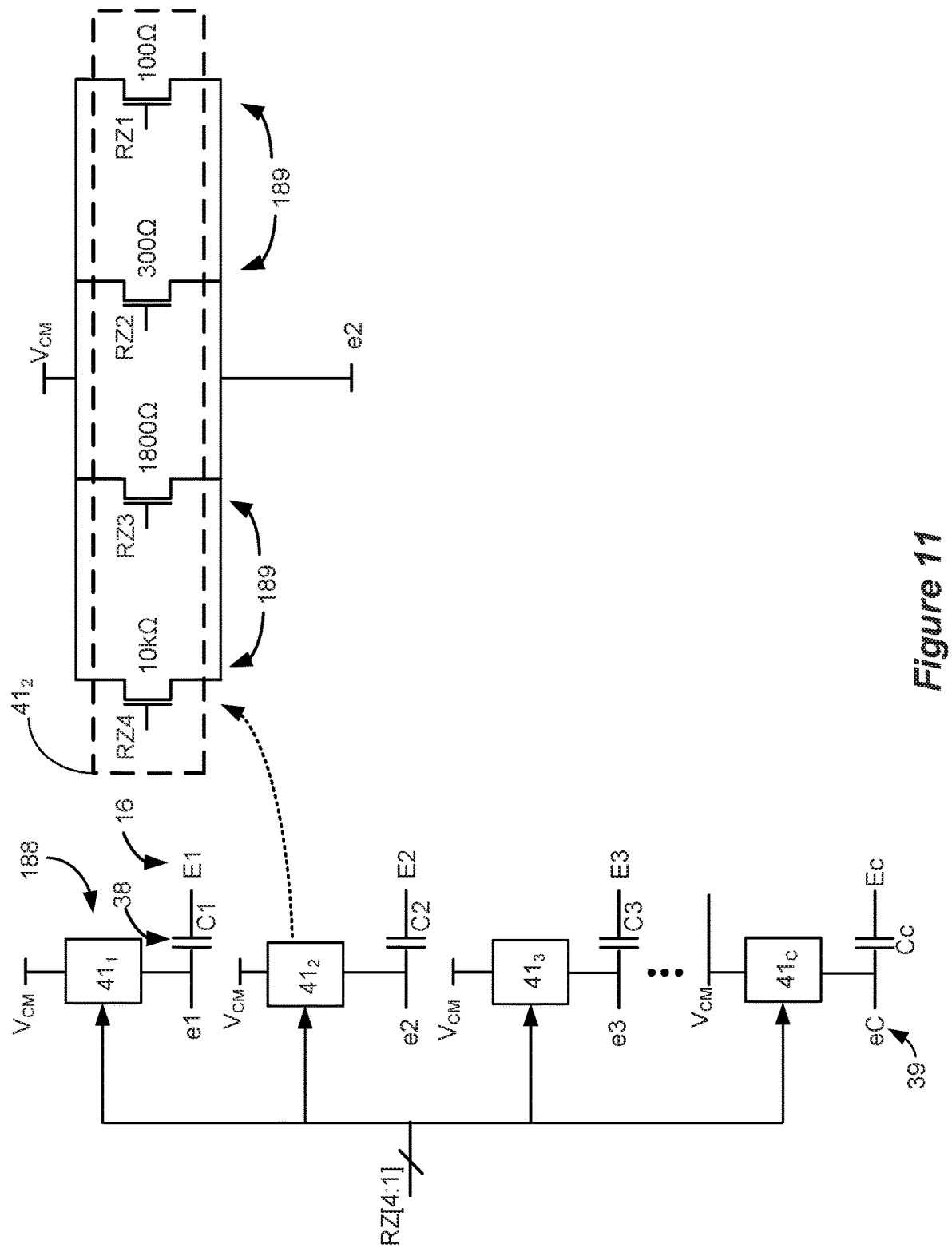
FIG. 11 shows aspects of a passive charge recovery circuitry for providing adjustable impedance during passive charge recovery.

FIG. 11 shows a subset of electrodes comprising electrodes E1-E3 and the case electrode Ec. Passive charge recovery switching circuits $41_i$ are connected between the electrode nodes ei 39 and a common reference voltage $V_{CM}$. As mentioned above, $V_{CM}$ may be VH/2, Vbat, ground (GND) or some other reference voltage value.

As mentioned above, the passive charge recovery switching circuits $41_i$ provide a variable resistance path between the electrode nodes ei and the common reference voltage $V_{CM}$ (the variable resistances were represented by the variable resistors 188 in FIG. 4). Each of the switching circuits $41_i$ receives each of four resistance control signals RZ[4:1] from the recovery logic/control 402, and thus any of these control signals can be asserted to set the resistance of the switching circuit $41_i$. The recovery impedance of each of the electrodes may be individually controlled, such that different impedances can be used on different electrodes at any given time. Thus, according to some embodiments, charge may be full recovered quickly on some electrodes while still presenting a high impedance to other electrodes (slower recovery).

In the embodiment illustrated in FIG. 11, the switching circuitry $41_2$ comprises four resistance transistors 189 connected in parallel between the electrode node e2 and the common reference voltage (e.g., $V_{CM}$). The resistance control signals RZ[4:1] are each received at the gate of one of the resistance transistors 189. Each of resistance transistors 189 is preferably sized differently to provide a different resistance. For example, this sizing difference can be realized by constructing each of the resistor transistors 189 with different lengths (e.g., 100×, 300×, 1800×, and 10000×). Likewise, the transistors widths could be sized as well to provide different resistances. In the example shown, RZ1 controls a resistance transistor 189 of 100 ohms; RZ2 controls 300 ohms; RX3 controls 1800 ohms; and RZ4 controls 10000 ohms. It will be appreciated that these resistance values are only exemplary and other resistance values could be chosen. As mentioned above, further aspects of varying the impedance during passive charge recovery are described in the incorporated U.S. Patent Application Publication No. 2018/0071527.

Figure 12:
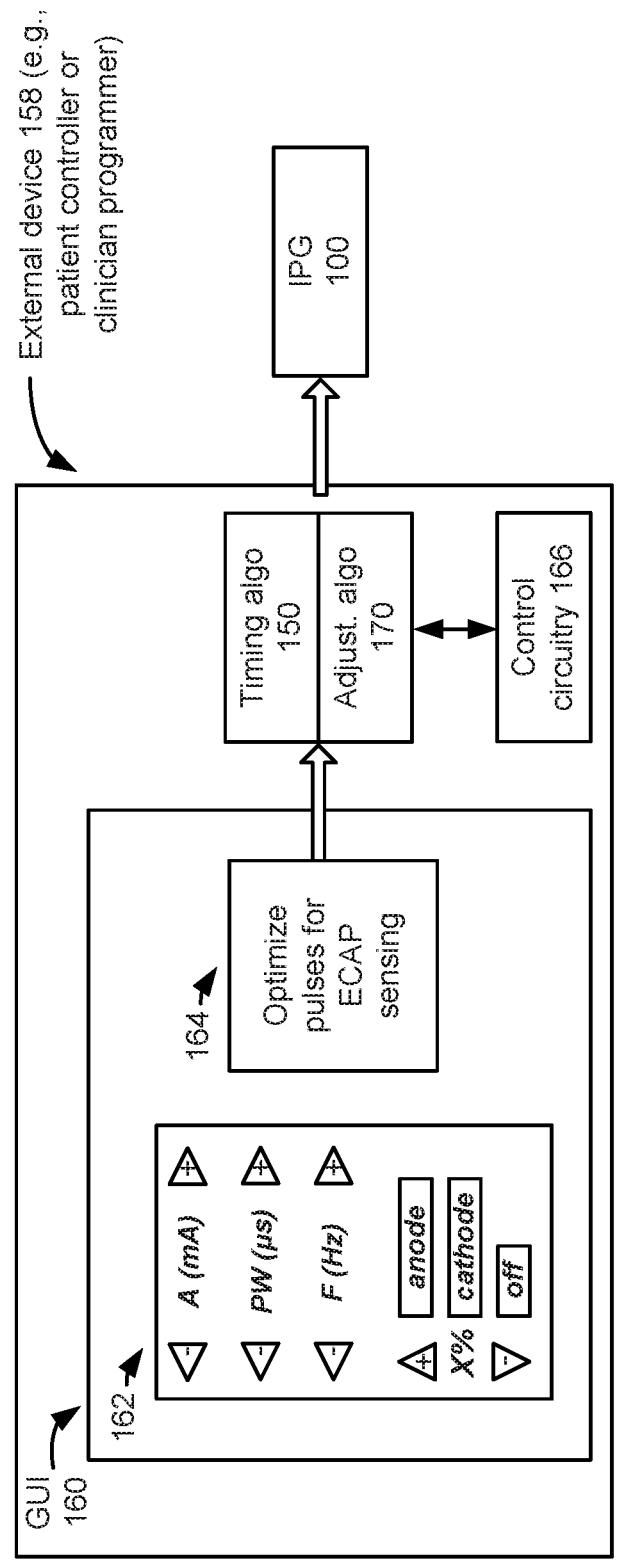
FIG. 12 shows operation of the timing and adjustment algorithms in an external device in communication with the IPG.

As shown in FIG. 4, the timing and adjustment algorithms can comprise part of the ECAP algorithm 124 operable in the control circuitry 102 (FIG. 4). However, these algorithms can also operate in whole or in part in external computer devices 158 (see FIG. 12, e.g.) that are used to program the IPG, such as a patient's external controller or a clinician programmer. Such external devices 158 typically wirelessly communicate with an IPG 100, and are described in U.S. Patent Application Publication 2019/0046800, which is incorporated herein by reference in its entirety. A Graphical User Interface (GUI) 160 as rendered on such an external device 158 is shown in FIG. 12. Shown in GUI 160 are user selectable options 162 to set stimulation parameters for the pulses or pulse phases of IPG, such as amplitude (A), pulse width (PW), and frequency (F), as well as whether certain electrodes are to operate as anodes or cathodes, and a percentage of the amplitude (X %) to be applied to that electrode. In reality, the GUI 160 and 162 may be much more complicated than what is shown.

The GUI 160 can include an option 164 to modify pulses otherwise prescribed into pulses better suited to ECAP sensing—such as by adding a multiple-impedance passive charge recovery phase, or modifying an already—prescribed passive charge recovery phase so that a high-impedance phase of passive charge recovery overlaps with the ECAP at the sensing electrode as shown in FIG. 8. Selection of option 164 may use the timing and adjustment algorithms of FIG. 9-10, or other algorithms, to determine the necessary pulse/recovery parameters to achieve this goal, and to send these parameters to the IPG. If necessary, the IPG may communicate ECAP test measurements back to the algorithms, such as ECAP start and finish times t1 and t2 as measured at the sensing electrodes S+/S−. The algorithms can be stored in non-transitory machine-readable media in the external device 158, such in as magnetic, optical, or solid-state memories, which may be stored in association with the external device 158's control circuitry 166, which may comprise one or more microcontrollers, microprocessors, FPGAs, DSPs, etc. In one example, control circuitry 166 can comprise one of the i5 family of microprocessors, as manufactured by Intel Corp.

Figure 13A:
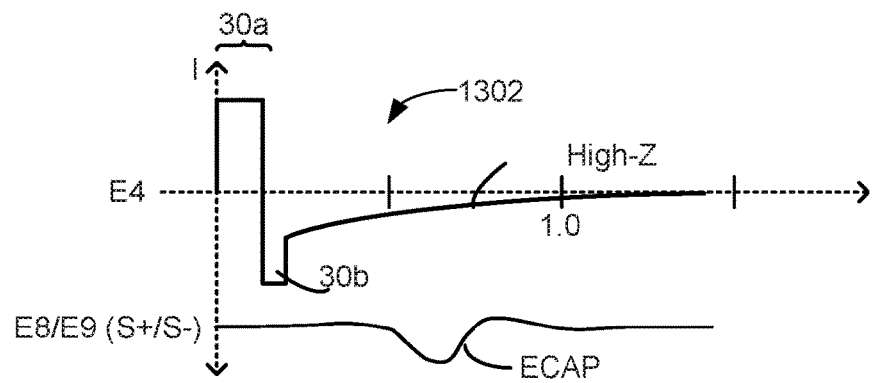
FIGS. 13A-13C show different examples in which the neural response can be sensed during a high-impedance passive charge recovery duration.
Figure 13B:
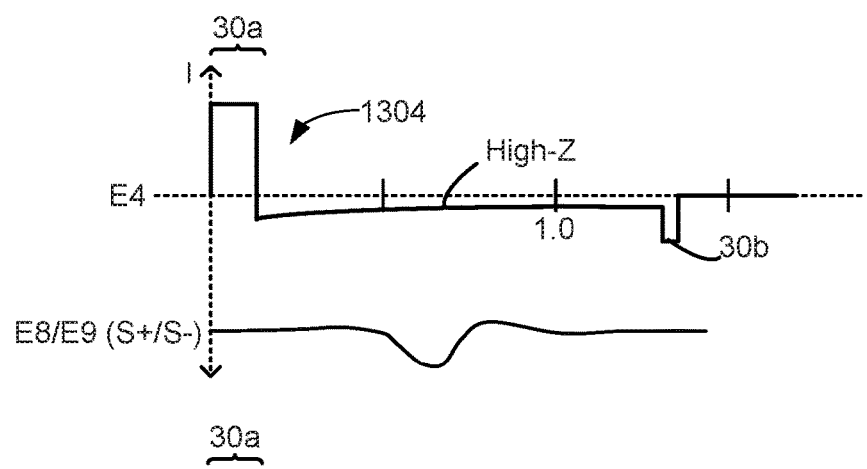
Figure 13C:
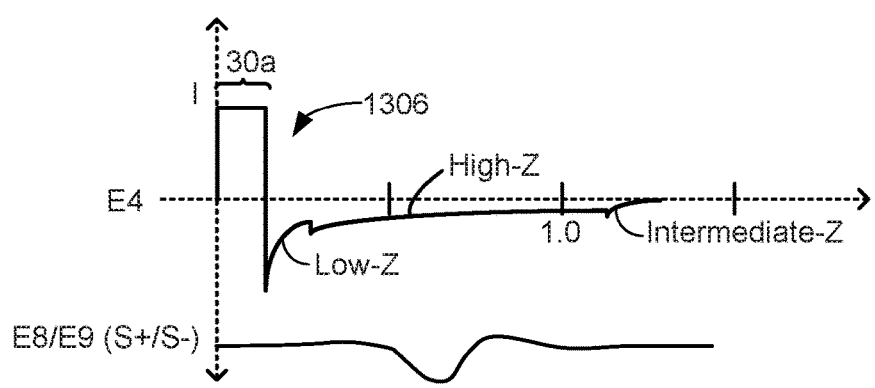

It will be appreciated that the methods and systems disclosed herein provide sensing of ECAPs or other neural responses during passive charge recovery by providing a high-impedance passive charge recovery during the neural response duration. The example illustrated in FIG. 8 focused on the provision of a monophasic stimulation pulse followed by a multi-impedance passive charge recovery comprising three impedance durations stepped from high-impedance to low impedance. Generally, the preference is to sense the ECAP during the high-impedance duration of the passive charge recovery, for the reasons explained above. It was mentioned above that other, more complex waveforms can be implemented according to the sensing/passive charge recovery strategies disclosed herein. FIGS. 13A-13C illustrate some examples of such more complex waveforms that utilize a high-impedance passive charge recovery phase during ECAP sensing.

FIG. 13A illustrates a waveform 1302 having a stimulation pulse having a stimulation phase 30a applied at a stimulation electrode (e.g., E4) followed by an active charge recovery phase 30b applied at the same electrode. Notice that the active charge recovery phase 30 b is not sufficient to recover all of the charge stored during stimulation pulse. Prior to the time that the ECAP arrives at the sensing electrodes S+/S− (e.g., E8/E9), charge recovery switches from active recovery to passive recovery using a high-impedance passive charge recovery to recover the remaining stored charge and the neural response is sensed during the high-impedance passive charge recovery duration.

FIG. 13B illustrates a waveform 1304, wherein a stimulation phase 30a is followed by a high-impedance passive charge recovery interval during the time at which the ECAP is present at the sensing electrodes. Following the high-impedance passive charge recovery interval and the sensing of the ECAP, a further active charge recovery phase 30b is used to recover the remaining charge.

FIG. 13C illustrates a waveform 1306, wherein a stimulation phase 30a is followed by an initial low-impedance passive charge recovery duration. Passive charge recovery is switched to a high-impedance passive charge recovery duration during the time at which the ECAP is measured. A further passive charge recovery (e.g., intermediate-impedance) can be used following ECAP sensing to recover the remaining charge. It should be noted that the waveforms 1302, 1304, and 1306 are just a few examples of waveforms contemplated by this disclosure. Generally, according to the disclosure, any combination of active and passive charge recovery can be used wherein the ECAP is sensed during a passive charge recovery phase, preferably, during a high-impedance passive charge recovery duration.

As noted earlier, an ECAP is just one example of a neural response that can be sensed using the disclosed techniques.

Although particular embodiments of the present invention have been shown and described, the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for operating a stimulator device, the stimulator device comprising a plurality of electrode nodes, each electrode node configured to be coupled to one of a plurality of electrodes configured to contact a patient's tissue, the method comprising:

providing actively-driven stimulation at at least one stimulation node selected from the plurality of electrode nodes, wherein the stimulation comprises at least one pulse comprising at least a first phase;

providing passively-driven passive charge recovery for a passive charge recovery duration, selecting a first recovery impedance for a high-impedance portion of the passive charge recovery duration and a second recovery impedance for a low-impedance portion of the passive charge recovery duration, wherein the first recovery impedance is greater than the second recovery impedance, using a variable resistance circuitry of the stimulator device to provide the selected recovery impedances during the passive charge recovery duration, determining a time at which the neural response will be present at the sensing electrode node and timing the passive charge recovery duration so that the high-impedance passive charge recovery portion will overlap the time at which the neural response will be present the sensing electrode node, and sensing an evoked neural response evoked by the stimulation during the high-impedance passive charge recovery portion at at least one sensing electrode node selected from the plurality of electrode nodes during the passive charge recovery duration.

2. The method of claim 1, wherein the variable resistance circuitry comprises a plurality of switching circuits, wherein each of the plurality of switching circuits is coupled with a different one of the electrode nodes and is configured, when selected, to provide variable impedance between its respective electrode node and a common node.

3. The method of claim 2, wherein the common node comprises a reference voltage selected from the group consisting of a battery voltage, a compliance voltage, a fraction of a compliance voltage, and ground.

4. The method of claim 2, wherein each of the plurality of switching circuits comprises a plurality of switches wherein the switches are selectable to vary the resistance.

5. The method of claim 2, wherein plurality of switches comprises a plurality of transistors in parallel.

* * * * *